United States Patent
Dotan et al.

(10) Patent No.: US 7,608,414 B2
(45) Date of Patent: *Oct. 27, 2009

(54) METHOD FOR DIAGNOSING AND PROGNOSING INFLAMMATORY BOWEL DISEASE AND CROHN'S DISEASE

(75) Inventors: Nir Dotan, Shoham (IL); Avinoam Dukler, Moddi'in (IL); Rom T. Altstock, Kfar-Saba (IL)

(73) Assignee: Glycominds, Ltd (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/351,185

(22) Filed: Feb. 8, 2006

(65) Prior Publication Data

US 2006/0205014 A1    Sep. 14, 2006

(51) Int. Cl.
G01N 33/53 (2006.01)
G01N 33/543 (2006.01)

(52) U.S. Cl. ............... 435/7.95; 435/7.1; 435/7.31; 435/7.92; 435/255.2; 435/287.2; 435/942; 436/503; 436/513; 436/518; 436/172; 436/811

(58) Field of Classification Search ............... 435/6, 435/7.1, 7.24, 7.31, 7.92, 7.95, 40.5, 255.2, 435/287.2, 942; 436/503, 513, 518, 172, 436/811
See application file for complete search history.

(56) References Cited

U.S. PATENT DOCUMENTS

| | | | |
|---|---|---|---|
| 5,443,952 A * | 8/1995 | Pestronk | 435/7.1 |
| 5,932,429 A | 8/1999 | Targan et al. | 435/7.24 |
| 6,033,864 A | 3/2000 | Braun et al. | 435/7.1 |
| 6,074,835 A | 6/2000 | Braun et al. | 435/7.211 |
| 6,218,129 B1 | 4/2001 | Walsh et al. | 435/7.21 |
| 6,294,321 B1 * | 9/2001 | Wakshull et al. | 435/4 |
| 7,109,182 B2 * | 9/2006 | Esnault et al. | 514/61 |
| 2003/0143649 A1 | 7/2003 | Boone et al. | 435/7.31 |
| 2004/0053263 A1 * | 3/2004 | Abreu et al. | 435/6 |

FOREIGN PATENT DOCUMENTS

| | | |
|---|---|---|
| WO | WO 92/16837 | 10/1992 |
| WO | WO 00/49412 | 8/2000 |
| WO | WO 01/40796 | 6/2001 |
| WO | WO 02/064556 A2 | 8/2002 |
| WO | WO 2004/015420 A1 | 2/2004 |

OTHER PUBLICATIONS

Main et al., 1988. Antibody to *Saccharomyces cerevisiae* (baker's yeast) in Crohn's disease. British Medical Journal 297: 1105-1106.*
Linskens et al., 2002. Evaluation of serological markers to differentiate between ulcerative colitis and Crohn's disease: pANCA, ASCA and agglutinating antibodies to anaerobic coccoid rods. Eur. J. Gastroenterol. Hepatol. 14: 1013-1018.*
Dotan et al., 2004. Anti-laminaribioside carbohydrate antibodies (ALCA) detected by a novel glycan microarray chip differentiate between Crohn's disease and ulcerative colitis patients. Gastroenterol. 126 (4, Suppl. 2): A203.*
Krause et al., 2002. Anti-*Saccharomyces cerevisiae* antibodies—a novel serologic marker for Behcet's disease. Clinical and Experimental Rheumatology 20 (Suppl. 26): S21-S24.*
Damoiseaux et al., 2002. Diagnostic value of anti-*Saccharomyces cerevisiae* and antineutrophil cytoplasmic antibodies for inflammatory bowel disease: high prevalence in patients with celiac disease. Journal of Clinical Immunology 22: 281-288.*
Quinton et al., 1998. Anti-*Saccharomyces cerevisiae* mannan antibodies combined with antineutrophil cytoplasmic autoantibodies in inflammatory bowel disease: prevalence and diagnostic role. Gut 42: 788-791.*
Vavassori et al., 2004. CARD15 mutation analysis in an Italian population. Leu1007fsinsC but neither Arg702Trp nor Gly908Arg mutations are associated with Crohn's disease. Inflammatory Bowel Dis. 10(2): 116-121.*
Hirschhorn et al., 2002. A comprehensive review of genetic association studies. Genetics in Medicine 4(2): 45-61.*
Ioannidis et al., 2001. Replication validity of genetic association studies. Nature Genetics 29: 306-309.*
Banin et al. *Glycosci. Glycotechnol.*, 14(77):127-137 (2002).
Bao *J. Chromatogr. B. Biomed. Sci.*, 699:463-480 (1997).
Brokroelofs et al. *Dig. Dis. Sci.*, 39:545-549 (1994).
Cambridge et al. *Gut*, 33:668-674 (1992).
Hou et al. *J. Immunol.*, 17:4373-4370 (2003).
Pool et al. *Gut*, 34:46-50 (1993).
Rongen et al. *J. Immunol. Meth.*, 204:105-133 (1997).
Saxon et al. *J. Allergy Clin. Immunol.*, 86:202-210 (1990).
Schwarz et al. *Glycobiol.*, 13(11):749-754 (2003).
Sendid et al. *Clin. Diagnostic Lab. Immunol.*, 3(2):219-226 (1996).
Wang et al. *Proteomics*, 3:2167-2175 (2003).

* cited by examiner

*Primary Examiner*—Ann Y Lam
*Assistant Examiner*—James L Grun
(74) *Attorney, Agent, or Firm*—Mintz, Levin, Cohn, Ferris, Glovsky and Popeo PC; Ivor R. Elrifi; Ingrid A. Beattie

(57) ABSTRACT

Disclosed are methods for diagnosing and prognosing Inflammatory Bowel disease or Crohn's disease (CD) by measuring levels of antibodies to glycans in a biological sample.

10 Claims, 7 Drawing Sheets

Figure 3 – ROC curves differentiating between CD patients with complicated diseases and CD patients non-complicated disease course according to combination of gASCA and CARD15 variants and according to the combination of gASCA, ACCA, ALCA and CARD15 variants.
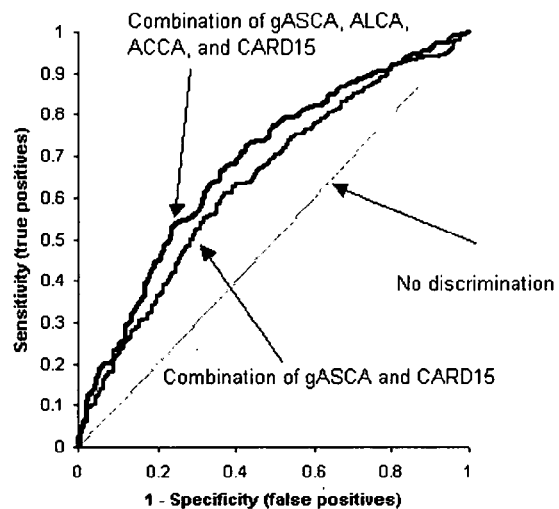

Figure 4 – ROC curves for differentiation between IBD patients (n= 1225) and non IBD patients (n=313) according to combination of gASCA, ACCA, ALCA, AMCA, and CARD15 variants. Versus gASCA alone.
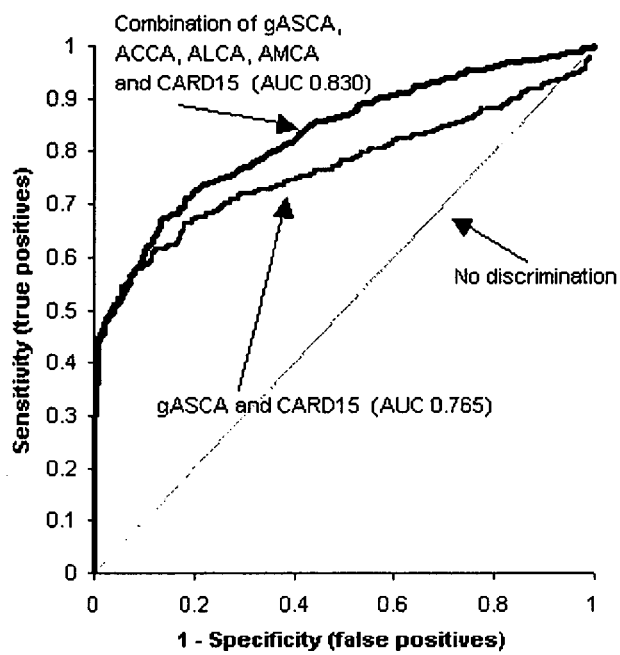

Figure 5 – Levels of anti-laminarin IgG antibodies in CD (n=133), UC (n=75) and IBS (n=22) patients.
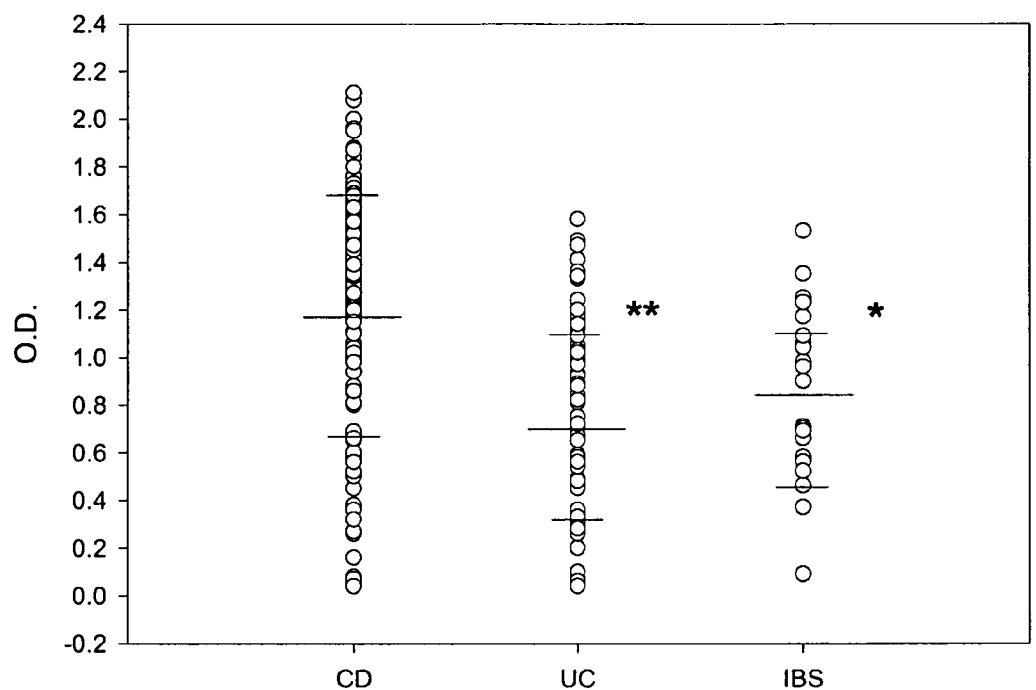
\* p =0.01 vs CD
\*\* p <0.0001 vs CD Figure 6 – ROC curves for differentiation between CD patients ( n= 133) and UC (n=75) according to anti-laminarin IgG and ALCA levels.
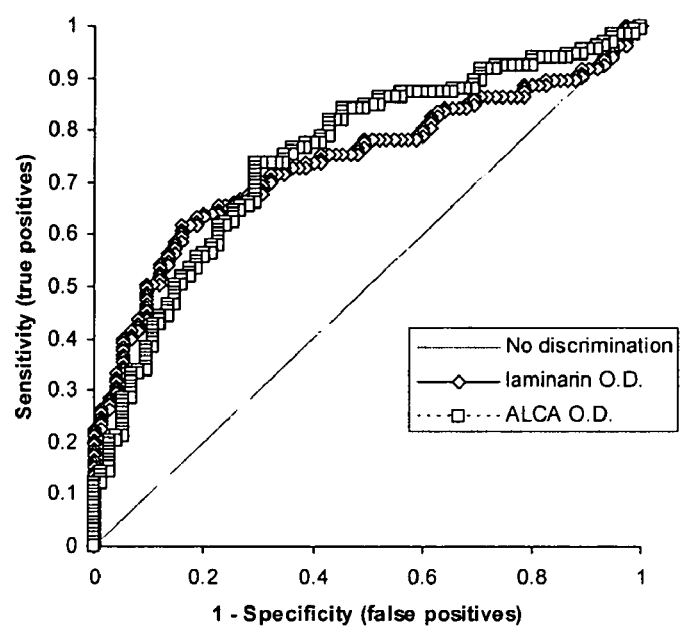

Figure 7 – Correlation between ALCA IgG and anti-laminarin IgG antibodies in CD patients ( n= 133) and UC (n=75).
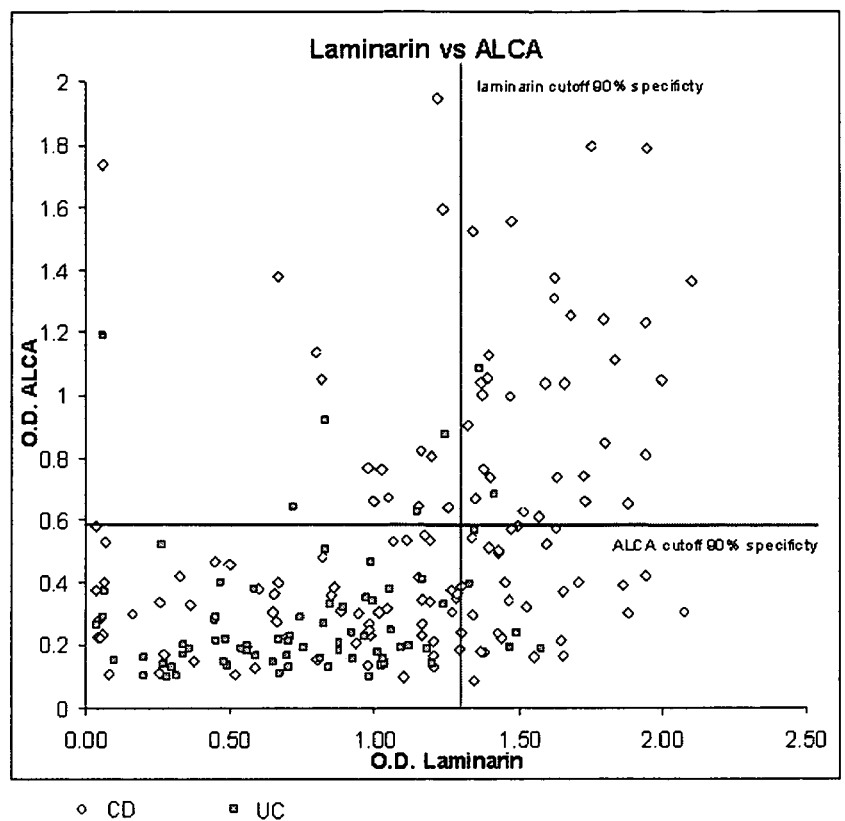

METHOD FOR DIAGNOSING AND PROGNOSING INFLAMMATORY BOWEL DISEASE AND CROHN'S DISEASE

RELATED APPLICATIONS

This application claims the benefit of, and priority to, U.S. Ser. No. 10/843,033, filed May 11, 2004, which in turn claims the benefit of, and priority to, U.S. Ser. No. 10/728,227, filed Dec. 3, 2003. The contents of these applications are incorporated by reference in their entireties.

FIELD OF THE INVENTION

The invention relates generally to a method for diagnosing and/or predicting the prognosis of digestive diseases such as Inflammatory Bowel Disease (IBD), Crohn's disease (CD) and CD subtypes, as well as CD complications by detecting levels of antibodies to glycans in a subject.

BACKGROUND OF THE INVENTION

Inflammatory bowel disease (IBD), which occurs worldwide and afflicts millions of people, is the collective term used to describe several gastrointestinal disorders of unknown etiology: Crohn's disease (CD), ulcerative colitis (UC) and Indeterminate Colitis (IC). IBD, Celiac disease and irritable bowel syndrome (IBS) will affect one-half of all Americans during their lifetimes, at a cost of several billion dollars. A primary determinant of these high medical costs is the difficulty of diagnosing digestive diseases. The cost associated with IBD and IBS is compounded by lost productivity, with persons suffering from these disorders missing an average of at least eight more days of work annually than persons not suffering from these disorders.

Symptoms associated with IBD, CD, UC, IC and IBS include, e.g., abdominal pain, chronic diarrhea, rectal bleeding, weight loss and cramping. These symptoms occur in very similar forms in IBD (i.e., CD or UC or IC), as well as in irritable bowel syndrome or other non-IBD bowel diseases. This makes a definitive diagnosis of IBD, CD or UC extremely difficult. In fact, only about one-tenth of the several million people suspected of suffering from CD are actually diagnosed with the disease.

The difficulty in differentially diagnosing IBD or CD from other digestive diseases like IBS hampers early and effective treatment of these diseases. In addition, Crohn's disease does not have a constant appearance. It varies according to locations, behaviors, severities and activities.

SUMMARY OF THE INVENTION

The invention is based in part on the discovery that patients with Inflammatory Bowel Disease, or Crohn's disease (CD) subtype, have elevated serum levels of certain IgG, IgA, and IgM isotype antibodies specific for certain glycan structures, as compared to the serum levels of these antibodies in healthy individuals, or individuals with IBS other types of gastrointestinal diseases.

Among the advantages of the invention is a highly sensitive and specific serological testing method for definitively distinguishing IBD patients from those with other digestive diseases, distinguishing patients with CD from UC, and for distinguishing CD patients with complicated disease from CD patients with less severe disease. The discrimination offered by the methods of the invention considerably shortens the time for initiating appropriate treatment and reduces significantly the amount of time and number of other procedures a patient must undergo until a diagnosis is made.

A further advantage of the invention is a panel of serological antibodies to certain sugar structures that provide these three different levels of information: first, whether or not a patient has IBD: second, if a patient does not have IBD, whether the patient has Crohn's disease; and third, for a patient that is diagnosed with Crohn's disease the severity and complications of the disease. This information can considerably shorten the period time for initiating appropriate treatment as well as reduce significantly the amount of time and number of procedures a patient will undergo until his diagnosis is accomplished. This facilitates earlier and more appropriate therapeutic intervention and minimizing uncertainty for patients and their families.

In one aspect, the invention provides a method of diagnosing IBD or Crohn's disease or predicting CD complications in a subject by providing a test sample from the subject and detecting in the test sample at least one of the following anti-glycan antibodies: an anti β-Glc antibody, an anti-Glc(β1,4)Glc(β) antibody, an anti-Glc(β1,3)Glc(β) antibody, an anti-Glc(β1,6)Glc(β) antibody, an anti-β-GlcNAc 6-sulfate antibody, an anti-Dextran antibody, an anti-Xylan antibody, an anti-GlcNAc(β1,4)GlcNAc(β) antibody, an anti-β-Gal 3-sulphate antibody, an anti-GlcNAc(β1,3)GalNAc(β) antibody, an anti-GlcNAc(β1,3)Gal(β1,4)Glc(β) antibody, an anti-α-Gal antibody, an anti-Gal(β) antibody, an anti-GalNAc(α)antibody, an anti-β-GalNAc antibody, an anti-α-Glc antibody, an anti-Gal(β1,6)Gal(β) antibody, an anti-Laminarin antibody, and an anti-GlcNAc(β1,6)GalNAc(α) antibody. The presence of one or more of the antibodies in the test sample indicates the subject has Crohn's disease.

In some embodiments, levels of the anti-glycan antibody or antibodies in the test sample are compared to the levels of anti-glycan antibodies in a control sample. The control sample is chosen from a group that includes one or more individuals known to have or not to have a gastrointestinal disorder, or to have or not to have a gastrointestinal disorder other than Crohn's disease. When the control sample is from an individual or individuals that do not have Crohn's disease, or has a gastrointestinal disease other than Crohn's disease, elevated levels in the test sample relative to the control sample indicates that the subject has Crohn's disease.

In some embodiments, the control sample is from one or more individuals with a gastrointestinal disorder that is irritable bowel syndrome, ulcerative colitis or other digestive diseases. In some embodiments, the control sample is from one or more individuals that do not have a gastrointestinal disorder.

In some embodiments, the control sample is from one or more individuals with a Crohn's disease with inflammation type of disease not suffering from fistulas or structuring disease.

In some embodiments, the control sample is from one or more individuals with a Crohn's disease that not underwent surgery.

In various embodiments, at least 2, 3, 4, 5, 6, 7, 8, 9, 10, 11, 12, 13, 14, or all of these antibodies are detected.

In some embodiments, the method further includes determining whether the test sample has an anti-Mannan antibody, which is also known as an anti-*Saccharomyces cerevisiae* antibody (ASCA). The presence of the anti-Mannan antibody in the sample indicates the subject has Crohn's Disease.

In some embodiments, the method further includes determining whether the test sample has an anti-neutrophil cytoplasmic antibody (ANCA). The presence of ANCA indicates the subject has IBD, may have Ulcerative Colitis, but probably does not have does not have Crohn's Disease.

The test sample can be, e.g., a biological fluid. Examples of biological fluids include, e.g., whole blood, serum, plasma, spinal cord fluid, urine, or saliva.

In some embodiments, one, two, three, four or all five of an anti-Glc(β1,3)Glc(β) antibody, an anti-Man(α1,3)Man(α) antibody, an anti Man(α1,3)[Man(α1,6)]Man(α) antibodies, anti-α-Man and/or anti-Mannan antibodies are detected.

The method can optionally include determining the isotype of the antibody. For example the method can include determining whether the antibody is an IgM, IgA, or IgG-type antibody. In some embodiments, the method is used to identify and compare one or more of an anti-Glc(β)IgG antibody, an anti-Glc(β1,3)Glc(β) IgG antibody, an anti-Glc(β1,6)Glc(β) IgG antibody, an anti-β-GalNAc antibody, an anti-α-GalNAc antibody, an anti-Glc(β1,4)Glc(β) IgG antibody, an anti-β-GlcNAc 6-sulfate IgG antibody, an anti-α-Man IgG antibody, an anti-Man(α1,3)[Man (α1-6)] Man(β) IgG antibody, an anti-Man(α1,3)Man(α) IgG antibody, an anti-Mannan IgG antibody an anti-Mannan IgA antibody, an anti-Laminarin antibody, an anti-Xylan IgG antibody, or an anti-Man(α1,2)Man(α) IgG antibody.

In some embodiments, a subject is scored as having CD if the test sample has elevated levels of one or more of an IgG anti-Glc(β1,3)Glc(β), IgG anti-Man(α1,3) Man(α), IgG anti Mannan (ASCA) antibodies, or IgA anti Mannan (ASCA) antibodies, but does not have elevated levels of ANCA.

In some embodiments, a subject is scored as having IBD if the test sample has elevated levels of IgG anti-Glc(β1,3)Glc(β), IgG anti anti-Man(α1,3)Man(α), IgG anti Mannan (ASCA) antibodies, IgA anti Mannan (ASCA) antibodies, or ANCA.

In some embodiments, the anti-glycan antibody or antibodies are detected using a fluorescent antibody, or are detected using an enzyme-linked immunoabsorbent assay (ELISA).

The test sample can be, e.g., a biological fluid. Examples of biological fluids include, e.g., whole blood, serum, plasma, spinal cord fluid, urine, or saliva.

The method can optionally include determining the isotype of the antibody. For example the method can include determining whether the antibody is an IgM, IgA, or IgG-type antibody.

In another aspect, the invention provides a method for diagnosing Crohn's disease in a subject. The method includes providing a test sample from a subject and determining whether an anti-glycan antibody is present in the test sample. At least one anti-glycan antibody is an IgG Glc(β1,3)Glc(β) antibody or an IgG anti-Man(α1,3)Man(α) antibody. The presence of at least one antibody in the test sample indicates the subject has Crohn's disease.

In some embodiments, levels of the anti-glycan antibody or antibodies in the test sample are compared to the levels of anti-glycan antibodies in a control sample. The control sample is chosen from a group that includes one or more individuals known to have or not to have a gastrointestinal disorder, or to have or not to have a gastrointestinal disorder other than Crohn's disease. When the control sample is from an individual or individuals that do not have Crohn's disease, or has a gastrointestinal disease other than Crohn's disease, elevated levels in the test sample relative to the control sample indicates that the subject has Crohn's disease.

In some embodiments, the control sample is from one or more individuals with a gastrointestinal disorder that is irritable bowel syndrome or ulcerative colitis or other digestive diseases. In some embodiments, the control sample is from one or more individuals that do not have a gastrointestinal disorder.

In a further aspect, the invention provides a method of differentially diagnosing Crohn's disease or inflammatory bowel disease in a subject. The method includes providing a test sample from a subject and determining whether the sample has an antibody that is an anti-neutrophil cytoplasmic antibody (ANCA), an IgG anti-Glc(β1,3)Glc(β)antibody, an IgG ASCA and/or IgA ASCA. The absence of ANCA and the presence of at least one of the IgG anti-Glc(β1,3)Glc(β) IgG ASCA, and IgA ASCA antibodies in the test sample indicates the subject has Crohn's disease, and the presence of at least one of the antibodies in the test sample indicates the subject has inflammatory bowel disease (IBD).

In some embodiments, the anti-glycan antibody or antibodies are detected using a fluorescent antibody, or are detected using an enzyme-linked immunoabsorbent assay (ELISA).

The test sample can be, e.g., a biological fluid. Examples of biological fluids include, e.g., whole blood, serum, plasma, spinal cord fluid, urine, or saliva.

The invention additionally provides a method of differentially diagnosing Crohn's disease colitis and ulcerative colitis in a subject. The method includes providing a test sample from a subject and determining levels of at least one an anti-glycan antibody in the sample. The anti-glycan antibody can be one or more of an IgG anti-Gal(α1,4)GlcNAc(α) antibody, an IgG anti-Gal(β1,4)GlcNAc(β) antibody, an IgG anti-α-GalNAc antibody, an IgG anti-α-Glc antibody, an IgG anti-β-Glc antibody, an IgG anti-β-GlcNAc(6-Sulphate) antibody, an IgG anti-β-GlcNAc antibody, an IgG anti-GlcNAc(β1,6)GalNAc(α) antibody, an IgA anti-Gal(α1,3)Gal(β1,4)GlcNAc(β1,3)Gal(β1,4)Glc(β)antibody, an IgA anti-Gal(β,1,4)Gal(β,1,4)Glc(β) antibody, an IgA anti-β-Gal antibody, an IgA anti-Gal(β1,3)[GlcNAc(β1,6)]GalNAc(α) antibody, an IgA anti-Gal(β1,3)GlcNAc(β) antibody, an IgA anti-Gal(β1,6)Gal(β) antibody, an IgA anti-GalNAc(α) antibody, an IgA anti-β-GalNAc antibody, IgA an anti-Glc(β) antibody, an IgA anti-Glc(β1,3)Glc(β) antibody, an IgA anti-β-GlcNAc antibody, an IgA anti-GlcNAc(β1,3)Gal(β1,4)Glc(β) antibody, an IgA anti-GlcNAc(β1,3)GalNAc(α) antibody, an IgA anti-GlcNAc(β1,4)GlcNAc(β) antibody, an IgA anti-GlcNAc(β1,6)GalNAc(α) antibody, and an IgA anti-β-Xyl antibody. The presence of the at least one antibody in the test sample indicates the subject has Crohn's disease colitis.

In some embodiments, the method further includes comparing the levels of the at least one anti-glycan antibody in the test sample to the levels of the at least one anti-glycan antibody in a control sample, wherein the control sample is selected from the group consisting of one or more individuals known to have or not to have Crohn's disease colitis or known to have or not to have ulcerative colitis (UC).

In some embodiments, the method includes determining whether an additional anti-glycan antibody or antibodies are present in the sample. The additional anti-glycan antibody can be one or more of an IgG anti-α-Gal antibody, an IgG anti-α-Man antibody, an IgG anti-Man(α1,3)Man(α1,6)Man(β) antibody, an IgG anti-Man(α1,3)Man(α1,6)Man(β) antibody, an IgG anti-Man(α1,3)Man(α) antibody, an IgA anti-Man(α) antibody, an IgA anti-Man(α1,2)Man(α) antibody, an IgA anti-Man(α1,3)Man(α1,6)Man(β) antibody, an IgA anti-Man(β1,3)Man(α) antibody, an IgA anti-Man(α1,6)Man(α) antibody, an IgA anti-β-Man antibody, and an IgA anti-α-Xyl antibody. The presence of the additional antibody or antibodies in the test sample indicates the subject has Crohn's disease colitis.

In some embodiments, the additional antibody or antibodies is an IgA anti-GlcNAc(β1,4)GlcNAc(β) antibody and/or and an IgG anti-Man(α1,3)Man(α) antibody.

In some embodiments, the method includes detecting at least two, three, four, five, six seven, eight, nine, ten, eleven or twelve of the antibodies.

In some embodiments, the test sample is a biological fluid (e.g., whole blood, serum, plasma, urine, or saliva).

In some embodiments, the anti-glycan antibody or antibodies are detected using a fluorescent antibody, or are detected using an enzyme-linked immunoabsorbent assay (ELISA).

The test sample can be, e.g., a biological fluid. Examples of biological fluids include, e.g., whole blood, serum, plasma, spinal cord fluid, urine, or saliva.

In a further aspect, the invention provides a method for diagnosing severe Crohn's disease in a subject. The invention includes providing a test sample from a subject with symptoms of Crohn's disease and determining whether the sample includes one or more of an anti-Glc(β1,3)Glc(β) antibody (ALCA), anti-Glc(β1,6)Glc(β) antibody, an anti-GlcNAc (β1,4)GlcNAc(β) antibody (ACCA), an anti-α-GalNAc antibody (AGCA), an anti-β-GalNAc antibody, and an anti-laminarin antibody. The presence of the antibodies in the test sample indicates the subject has severe Crohn's disease. In various embodiments, 1, 2, 3, 4, 5, 6, or 7 of the antibodies are detected.

In some embodiments, the method further includes determining whether the sample includes one or more of an anti mannan antibody (gASCA), an anti-Man(α1,3)Man(α) antibody (AMCA), an anti-Man(α1,6)Man(α) antibody (AMBA), an anti-Man(α1,2)Man(α) antibody (AMNA), and an anti-α-Man antibody (AMA). In various embodiments, 1, 2, 3, 4, or 5 of the antibodies are detected.

In some embodiments, the method includes further determining whether the sample includes an anti-neutrophil cytoplasmic antibody (ANCA).

In some embodiments, the method additionally includes determining whether the subject has a CARD15 allele associated with Crohn's disease. In some embodiments, the CARD15 allele is the R702W, G908R, or 1007fs CARD15 allele.

In some embodiments, the method includes further comprising determining whether the subject with severe Crohn's disease has strictures or fistulas.

In some embodiments, the method includes treating the subject with the antibodies for symptoms associated with severe Crohn's disease. In some embodiments, the treatment is surgery.

In some embodiments, one or more of the anti-Glc(β1,3) Glc(β) antibody (ALCA), anti-Glc(β1,6)Glc(β) antibody, the anti-α-GalNAc antibody (AGCA), and the anti-laminarin antibody are IgG antibodies and one or both of the anti-GlcNAc(β1,4)GlcNAc(β) antibody (ACCA) and the anti-β-GalNAc antibody are IgA antibodies.

In some embodiments, one or more of the gASCA) antibody, anti-Man(α1,3)Man(α) antibody (AMCA) antibody, anti-Man(α1,6)Man(α) antibody (AMBA), anti-Man(α1,2) Man(α) antibody (AMNA) and anti-α-Man antibody (AMA) are IgG antibodies.

In some embodiments, the test sample is serum.

In some embodiments, the presence of antibodies in the sample are determined using an enzyme-linked immunosorbent assay (ELISA).

In some embodiments, a subject is determined to have the indicated disease if the level of the measured antibody is above a cut-off value, which can be independently determined for each antibody. The cut-off values can be independently selected to achieve an optimized clinical parameter including, e.g., sensitivity, specificity, negative predictive value, positive predictive value and overall agreement.

Thus, in some embodiments, the subject is determined to have severe Crohn's disease if when the anti-β-GalNAc is above S, the anti-Glc(β1,6)Glc(β) antibody is above T, the ALCA level is above W, the AGCA is above X, the anti-laminarin antibody is above Y, and the ACCA level is above Z, where S, T, W, X, Y, and Z are selected to optimize sensitivity, specificity, negative predictive value, positive predictive value and overall agreement.

Similarly, in other embodiments, the subject is determined to have severe Crohn's disease, if when the gASCA level is above U, and the AMCA is above V, U and V are independently selected to achieve an optimized clinical parameter selected from the group consisting of: sensitivity, specificity, negative predictive value, positive predictive value and overall agreement. Additional variables (denoted by an aribitrary identifier such as a letter) can be assigned for assessing levels of other anti-glycan antibodies in the assays disclosed herein.

In other embodiments, the method comprises determining the aggregate amount of ALCA, anti-Glc(β1,6)Glc(β) antibody, AGCA, anti-β-GalNAc antibodies, anti-laminarin antibodies and ACCA, the subject is determined to have severe Crohn's disease if the aggregate amount of the antibodies is greater than R.

In other embodiments, the method includes determining the aggregate amount of ALCA, anti-Glc(β1,6)Glc(β) antibody, AGCA, anti-β-GalNAc anti-lamianarin antibodies and ACCA, the subject is determined to have severe Crohn's disease if the aggregate amount of the antibodies is greater than R.

In some embodiments, the method further comprises determining the aggregate amount of gASCA, AMCA, AMBA, AMNA and AMA antibodies, and the subject is determined to have severe Crohn's disease if the aggregate amount of the antibodies is greater than R.

In a still further aspect, the invention provides a method for assessing the prognosis of Crohn's disease complications in a subject by providing a test sample from a subject with symptoms of Crohn's disease, and determining whether the sample includes an anti-Glc(β1,3)Glc(β) antibody (ALCA), anti-Glc (β1,6)Glc(β) antibody an anti-GlcNAc(β1,4)GlcNAc(β) antibody (ACCA), an anti-α-GalNAc antibody (AGCA), an anti-β-GalNAc antibody, an anti-Glc(α1,6) Glc(α) antibody, and/or an anti-laminarin antibody. The presence of the antibodies in the test sample indicates a severe Crohn's disease prognosis for the subject.

In a further aspect, the invention provides a method for assessing the prognosis of Crohn's disease complications in a subject. The method includes providing a test sample from a subject with symptoms of Crohn's disease and determining whether the sample includes one or more of an anti-Glc(β1, 3)Glc(β) antibody (ALCA), an anti-GlcNAc(β1,4)GlcNAc (β) antibody (ACCA), an anti-Man(α1,3)Man(α) antibody (AMBA), and an anti-Mannan antibody. The presence of the antibodies in the test sample indicates a severe Crohn's disease prognosis for the subject.

In a further aspect, the invention features a method for differentiating inflammatory bowel disease (IBD) from a disease other than IBD in subject. The method includes providing a test sample from a subject with symptoms of IBD and determining whether the sample includes determining whether the sample includes one or more of an anti-Glc(β1, 3)Glc(β) antibody (ALCA), an anti-Glc(β1,6)Glc(β) antibody, an anti-GlcNAc(β1,4)GlcNAc(β) antibody (ACCA), an anti-α-GalNAc antibody (AGCA), an anti-β-GalNAc antibody, an anti-Glc(α1,6)Glc(α) antibody and an anti-Glc(α1,6)Glc(α) antibody, and an anti-laminarin antibody. The presence of the antibodies in the test sample indicates the subject has inflammatory bowel disease.

In some embodiments, the method includes determining whether the sample includes 2, 3, 4, 5, 6, 7, or 8 of an anti-Glc(β1,3)Glc(β) antibody (ALCA), an anti-Glc(β1,6)Glc(β) antibody, an anti-GlcNAc(β1,4)GlcNAc(β) antibody (ACCA), an anti-α-GalNAc antibody (AGCA), an anti-β-GalNAc antibody, an anti-Glc(α1,6) Glc(α) antibody, and/or an anti-laminarin antibody.

In some embodiments, the method further includes further comprising determining whether the sample includes one or more of an anti mannan antibody (gASCA), an anti-Man(α1,3)Man(α) antibody (AMCA), an anti-Man(α1,6)Man(α) antibody (AMBA), anti-Man(α1,2)Man(α) antibody (AMNA), and anti-α-Man antibody (AMA). In some embodiments, the method includes detecting 2, 3, 4, or 5 of these antibodies.

In some embodiments, the method further comprises determining whether the sample includes an anti-neutrophil cytoplasmic antibody (ANCA).

In some embodiments, the method includes further comprising determining whether the subject has a CARD15 allele associated with Crohn's disease. The allele can be, e.g., a R702W, G908R, or 1007fs CARD15 allele.

In some embodiments, the method includes further determining whether the subject with inflammatory bowel disease has strictures or fistulas.

In some embodiments, the method includes further treating the subject with the antibodies for symptoms associated with severe Crohn's disease. In some embodiments, the treatment is surgery.

In some embodiments, the anti-Glc(β1,3)Glc(β) antibody (ALCA), anti-Glc(β1,6)Glc(β) antibody, the anti-α-GalNAc antibody (AGCA), the anti-β-GalNAc, and/or the anti-laminarin antibody is an IgG antibody, and the anti-GlcNAc(β1,4)GlcNAc(β) antibody (ACCA) and/or the anti-β-GalNAc antibody is an IgA antibody.

In some embodiments, the gASCA antibody, anti-Man(α1,3)Man(α) antibody (AMCA) antibody, anti-Man(α1,6)Man(α) antibody (AMBA), anti-Man(α1,2)Man(α) antibody (AMNA) and/or or anti-α-Man antibody(AMA) is an IgG antibody.

In some embodiments, the anti-Glc(β1,3)Glc(β) antibody (ALCA), anti-Glc(β1,6)Glc(β) antibody, the anti-α-GalNAc antibody (AGCA), the anti-β-GalNAc antibody, and the anti-laminarin antibody are IgG antibodies and the anti-GlcNAc(β1,4)GlcNAc(β) antibody (ACCA) and the anti-β-GalNAc antibodies are IgA antibodies.

In some embodiments, the test sample is serum.

In some embodiments, the presence of antibodies in the sample are determined using an enzyme-linked immunosorbent assay (ELISA).

In some embodiments, the subject is determined to have severe Crohn's disease if when the ALCA level is above W, the AGCA is above X, the anti-laminarin antibody is above Y, and the ACCA level is above Z, wherein W, X, Y, and Z are independently selected to achieve an optimized clinical parameter selected from the group consisting of: sensitivity, specificity, negative predictive value, positive predictive value and overall agreement.

In some embodiments, the subject is determined to have severe Crohn's disease, if when the gASCA level is above U, and the AMCA is above V, where U and V are independently selected to achieve an optimized clinical parameter selected from the group consisting of: sensitivity, specificity, negative predictive value, positive predictive value and overall agreement.

In some embodiments, the method comprises determining the aggregate amount of ALGA, AGCA, anti-laminarin antibodies and ACCA, the subject is determined to have severe Crohn's disease if the aggregate amount of the antibodies is greater than T.

The invention additionally provides reagents for detecting anti-glycan antibodies that reveal the presence of Crohn's Disease. The reagents include one or more carbohydrates that specifically react with an anti-β-Glc antibody, an anti-Glc(β1,4)Glc(β) antibody, an anti-Glc(β1,3)Glc(β) antibody, an anti-Glc(β1,6)Glc(β) antibody, an anti-β-GalNAc antibody, an anti-α-GalNAc antibody, an anti-GlcNAc(β) 6-sulfate antibody, an anti-Man(α1,2)Man(α) antibody, an anti-Man(α1,3)Man(α) antibody, an anti-Man(α1,6)Man(α) antibody, an anti-Man(α) antibody, an anti-Man(α1,3)[Man(α1,6)]Man (α), an anti-Mannan antibody, an anti-Dextran antibody, an anti-Xylan antibody, an anti-GlcNAc(β1,4)GlcNAc(β) antibody, an anti-β-Gal 3-sulphate antibody, an anti-aGlcNAc (β1,3)GalNAc(β) antibody, an anti-GlcNAc(β1,3)Gal(β1,4)Glc(β) antibody, and/or an anti-Gal(α1,3)Gal(β1,4)GlcNAc (β) antibody. In some embodiments, the reagents are attached to a solid phase.

Also within the invention are arrays that include reagents (preferably carbohydrate reagents) that specifically detect the disease-detecting antibodies disclosed herein. For example, an array useful for detecting CD can include one or more reagents that detect an anti-β-Glc antibody, an anti-Glc(β1,4)Glc(β) antibody, an anti-Glc(β1,3)Glc(β) antibody, anti-Glc(β1,6)Glc(β) antibody, an anti-GlcNAc(β) 6-sulfate antibody, an anti-Man(α1,2)Man(α) antibody, an anti-Man(α1,3)Man(α) antibody, an anti-Man(α1,6)Man(α) antibody, an anti-α-Man antibody, an anti-Man(α1,3)[Man(α1,6)]Man (α), an anti-Mannan antibody, an anti-Dextran antibody, an anti-Xylan antibody, an anti-GlcNAc(β1,4)GlcNAc(β) antibody, an anti-Gal 3-sulphate(β) antibody, or an anti-Gal(α1,3)Gal (β1,4)GlcNAc(β) antibody.

In some embodiments, the reagents that are used to specifically bind and detect those anti glycans antibodies are the specific glycan structures. In other embodiments, the reagents are other molecules or macromolecules that include the specific glycan structure. The glycan or sugar structures can be only the a carbohydrate moiety (including monosaccharides an oligosaccharide or a polysaccharide) or displaying on any solid phase or other macromoleculeor any other molecular structure that includes the glycan. The glycan-containing structure can be naturally occurring, e.g., extracted from an organism, or synthetic.

For example, the anti-Glc(β1,3)Glc(β) antibody can be detected using the polysaccharide β-D(1,3) Glucan, a polymer of glucose units connected in a (β,1,3) glycosidic bond. Thus, the glycan itself can be used for detecting the corresponding antibody or antibodies, as can any carbohydrate, peptide, protein, or any other molecular structure that includes the glycan.

In some embodiments, the reagents that are used to specifically bind and detect the anti glycans antibodies of the invention are peptides that mimic the carbohydrate antigens of the invention. The peptides can be used to identify specific anti glycan antibodies.

The array may additionally include a reagent or reagent, e.g., a carbohydrate reagent or reagents, that detect an anti-Mannan (ASCA) antibody or a ANCA.

In some embodiments, the glycans are attached to the array via a linker. A suitable linker includes at least one ethylene glycol derivative, at least two cyanuric chloride derivatives and an anilino group.

In some embodiments, at least two of the reagent or reagents are provided at the same location on the addressable array.

In some embodiments, the array includes a reagent, e.g., a glycan reagent that detects an anti-Glc(β1,3)Glc(β) antibody and/or an IgG anti-Man(α1,3)Man(α) antibody.

Other arrays include arrays useful for differentially diagnosing Crohn's disease or inflammatory bowel disease in a subject. The array includes one or more reagents (e.g., glycan or peptide reagents) that detect an anti-neutrophil cytoplasmic antibody (ANCA), an anti-Glc(β1,3)Glc(β)antibody, an ASCA; or an ASCA. In some embodiments, the array includes, one, two, or three of these reagents.

The invention additionally provides an array of reagents (e.g., glycan or peptide reagents) useful for differentially diagnosing Crohn's disease colitis and ulcerative colitis in a subject. The arrays include one or more reagents that detect an anti-Gal(α1,4)GlcNAc(α) antibody, an anti-Gal(β1,4)GlcNAc(β) antibody, an anti-GalNAc(α) antibody, an anti-α-Glc antibody, an anti-β-Glc antibody, an anti-β-GlcNAc(6-Sulphate) antibody, an anti-β-GlcNAc antibody, an anti-GlcNAc(β1,6)GalNAc(α) antibody, an anti-Gal(α1,3)Gal(β1,4)GlcNAc(β1,3)Gal(β1,4)Glc(β) antibody, an anti-Gal(α1,4)Gal(β1,4) Glc(β) antibody, an anti-β-Gal antibody, an anti-Gal(β1,3)[GlcNAc(β1,6)]GalNAc(α) antibody, an anti-Gal(β1,3)GlcNAc(β) antibody, an anti-Gal(β1,6)Gal(β) antibody, an anti-α-GalNAc antibody, an anti-β-GalNAc antibody, an anti-β-Glc antibody, an anti-Glc(β1,3)Glc(β) antibody, an anti-β-GlcNAc antibody, an anti-GlcNAc(β1,3)Gal(β,1,4)Glc(β) antibody, an anti-GlcNAc(β1,3)GalNAc(α) antibody, an anti-GlcNAc(β1,4)GlcNAc(β) antibody, an anti-GlcNAc(β1,6)GalNAc(α)antibody, and an anti-Xyl(β) antibody.

In some embodiments, the array includes reagents that bind 2, 3, 4, 6, 6, 7, 8, 9, 10, 11, 12, 13, 14, 15, 16, 17, 18, 19, 20, 21, 22, 23, or 24 of these antibodies.

The array may additionally include a reagent, e.g., a glycan or peptide reagent, that detects an anti-Gal(α) antibody, an anti-Man(α) antibody, anti-Man(α1,3)Man(α1,6)Man(β) antibody, an anti-Man(α1,3)Man(α1,6)Man(β) antibody, an anti-Man(α1,3)Man(α) antibody, an anti-Man(α) antibody, an anti-Man(α1,2)Man(α) antibody, an anti-Man(α1,3)Man (α1,6)Man(β) antibody, an anti-Man(β1,3)Man(α) antibody, an an anti-Man(α1,6)Man(α) antibody, an anti-β-Man antibody, and/or an anti-α-Xyl antibody.

In some embodiments, the array includes reagents that bind 2, 3, 4, 6, 6, 7, 8, 9, 10, 11, or 12 of these antibodies.

The array may additionally include a reagent (e.g., a glycan or peptide reagent) that detects an anti-GlcNAc(β,1,4)GlcNAc(β) antibody and/or an anti-Man(α,1,3)Man(α) antibody.

Also provided by the invention is an array useful for differentially diagnosing inflammatory bowel disease (IBD) or non-IBD digestive disease (NIC). The array includes a reagent (e.g., a glycan or peptide reagent) that detects anti chitobioside (GlcNAc(β1,4)GlcNAc(β)) carbohydrate antibodies (ACCA) and/or anti-mannan (ASCA) antibodies. The array may optionally include a reagent that detects anti-laminarobioside (Glc(β1,3)Glc(β)) Carbohydrate Antibodies (ALCA).

The invention additionally provides kits that include reagents for detecting anti-glycan antibodies that reveal the presence of Crohn's Disease. The kits include one or more carbohydrate reagent(s) that specifically reacts with an anti-Glc(β) antibody, an anti-Glc(β1,4)Glc(β) antibody, an anti-Glc(β1,3)Glc(β) antibody, an anti-GlcNAc(β) 6-sulfate antibody, an anti-Man(α1,2)Man(α) antibody, an anti-Man(α1, 3)Man(α) antibody, an anti-Man(α,1,6)Man(α) antibody, an anti-α-Man antibody, an anti-Man(α1,3)[Man(α,1,6)]Man (α), an anti-Mannan antibody, an anti-Dextran antibody, an anti-Xylan antibody, an anti-GlcNAc(β1,4)GlcNAc(β) antibody, an anti-Gal 3-sulphate(β) antibody, an anti-aGlcNAc (β1,3)GalNAc(β) antibody, an anti-GlcNAc(β1,3)Gal(β,1-4) Glc(β) antibody, and/or an anti-Gal(α1,3)Gal(β1,4)GlcNAc (β) antibody. The kits may be provided in one or more containers. In some embodiments, the kits contain directions for using the kits to perform the methods described herein. The kits may optionally include reagents for detecting antibody isotypes (e.g., IgA, IgG, and IgM antibodies).

In some embodiments, the kits include reagents that are used to specifically bind and detect those anti glycans antibodies that are the specific glycan structures. In other embodiments, the reagents in the kits are other molecules or macromolecules that include the specific glycan structure. For example, the anti-Glc(β1,3)Glc(β) antibody can be detected using the polysaccharide β-D(1,3) Glucan, a polymer of glucose units connected in a (β1,3) glycosidic bond. Thus, the glycan itself can be used for detecting the corresponding antibody or antibodies, as can any carbohydrate, peptide, protein, or any other molecular structure that includes the glycan.

In some embodiments, the kits include reagents that are used to specifically bind and detect ASCA and/or ANCA.

Also provided by the invention are kits useful for differentially diagnosing Crohn's disease or inflammatory bowel disease in a subject. The kit includes one or more reagents (e.g., glycan or peptide reagents) that detect an anti-neutrophil cytoplasmic antibody (ANCA), an anti-Glc(β1,3)Glc(β)antibody, an ASCA; or an ASCA. In some embodiments, the kit includes, one, two, or three of these reagents.

The invention additionally provides a kit of reagents (e.g., glycan or peptide reagents) useful for differentially diagnosing Crohn's disease colitis and ulcerative colitis in a subject. The kits include one or more reagents that detect an anti-Gal (α1,4)GlcNAc(α) antibody, an anti-Gal(β1,4)GlcNAc(β) antibody, an anti-α-GalNAc antibody, an anti-α-Glc antibody, an anti-β-Glc, antibody, an anti-β-GlcNAc(6-Sulphate) antibody, an anti-β-GlcNAc antibody, an anti-GlcNAc(β1,6) GalNAc(α) antibody, an anti-Gal(α1,3)Gal(β,1,4)GlcNAc (β1,3)Gal(β1,4)Glc(β)antibody, an anti-Gal(α1,4)Gal(β1,4) Glc(β) antibody, an anti-β-Gal antibody, an anti-Gal(β1,3) [GlcNAc(β1,6)]GalNAc(α) antibody, an anti-Gal(β1,3) GlcNAc(β) antibody, an anti-Gal(β1,6)Gal(β) antibody, an anti-α-GalNAc antibody, an anti-β-GalNAc antibody, an anti-Glc(β) antibody, an anti-Glc(β1,3)Glc(β) antibody, an anti-GlcNAc(β) antibody, an anti-GlcNAc(β1,3)Gal(β1,4) Glc(β) antibody, an anti-GlcNAc(β1,3)GalNAc(α) antibody, an anti-GlcNAc(β1,4)GlcNAc(β) antibody, an anti-GlcNAc (β,1,6)GalNAc(α) antibody, and an anti-β-Xyl antibody In some embodiments, the kit includes reagents that bind 2, 3, 4, 6, 6, 7, 8, 9,10, 11, 12, 13, 14, 15, 16, 17, 18, 19, 20, 21, 22, 23, or 24 of these antibodies.

The kit may additionally include a reagent, e.g., a glycan or peptide reagent, that detects an anti-Gal(α) antibody, an anti-Man(α) antibody, anti-Man(α1,3)Man(α,1,6)Man(β) antibody, an anti-Man(α1,3)Man(α1,6)Man(β) antibody, an anti-Man(α1,3)Man(α) antibody, an anti-Man(α) antibody, an anti-Man(α1,2)Man(α) antibody, an anti-Man(α1,3)Man (α1,6)Man(β) antibody, an anti-Man(β1,3)Man(α) antibody, an anti-Man(α1,6)Man(α) antibody, an anti-β-Man antibody, and/or an anti-α-Xyl antibody. In some embodiments, the kit includes reagents that bind 2, 3, 4, 6, 6, 7, 8, 9, 10, 11, or 12 of these antibodies.

The kit may additionally include a reagent (e.g., a glycan or peptide reagent) that detects an anti-GlcNAc(β,1,4)GlcNAc (β) antibody and/or an anti-Man(α,1,3)Man(α) antibody.

Also provided by the invention is a kit useful for differentially diagnosing inflammatory bowel disease (IBD) or non-IBD digestive disease (NIC). The kit includes a reagent (e.g., a glycan or peptide reagent) that detects anti chitobioside (GlcNAc(β1,4)GlcNAc(β)) carbohydrate antibodies (ACCA) and/or anti-mannan (ASCA) antibodies. The kit may optionally include a reagent that detects anti-laminarobioside (Glc(β1,3)Glc(β)) Carbohydrate Antibodies (ALCA).

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 3 is ROC curves differentiating between CD patients with complicated diseases and CD patients non-complicated disease courses using a combination of gASCA and CARD15 variants, and using a combination of gASCA, ACCA, ALCA and CARD15 variants.

FIG. 4 are ROC curves comparing the prediction performance of the known predictors gASCA and CARD15 to the combination of ALCA, ACCA, gASCA and number of CARD15.

FIG. 5 are ROC curves comparing the diagnosis performance of the known predictors gASCA and CARD15 to the combination of ALCA, ACCA, gASCA and CARD15

FIG. 6 are ROC curves differentiating between CD patients (n=133) and UC (n=75) according to anti-laminarin IgG and ALCA IgG levels.

FIG. 7 shows ALCA IgG and anti-laminarin IgG antibodies in CD patients (n=133) and UC (n=75).

DETAILED DESCRIPTION OF THE INVENTION

Figure 1:
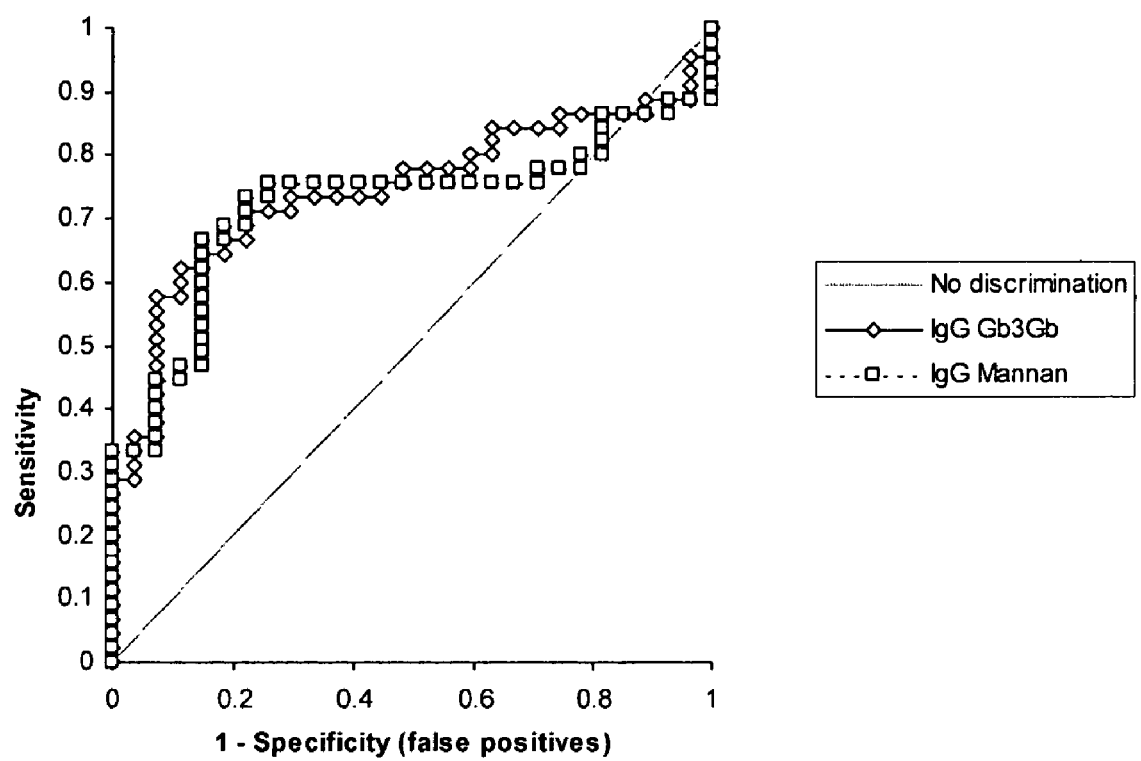
FIG. 1 is a graph showing a Receiver Operator Characteristic (ROC) curve for differentiation between individuals with CD and individuals with other digestive diseases using IgG anti-Glc(β1,3)Glc(β) (Gb3Gb) and IgG anti-Mannan antibodies

The invention provides methods for differentially diagnosing inflammatory Bowel Disease (IBD) patients (including Crohn's disease (CD), ulcerative colitis and indeterminate colitis) and non-IBD patients (including, for example, irritable bowel syndrome (IBS), Celiac disease or any other bowel condition which is not IBD) by examining a test sample from a subject for antibodies to one or more specific glycans. The presence of the antibodies in the test sample indicates the subject has IBD, CD and not disease other than IBD (such as IBS). In some embodiments, elevated levels of glycans in a test sample from the subject as compared to the levels of the glycan or glycans in a reference sample that does not have CD indicates that the subject has CD. The methods can be used distinguish the presence of CD in a subject from other inflammatory bowel diseases (including ulcerative colitis).

Certain antibodies to glycan structures are discussed herein. A translation of LinearCode™ syntax used to describe glycan structure in IUPAC nomenclature can be found in Table 1. The glycans are presented either in the International Union of Pure and Applied Chemistry (IUPAC) condensed form for nomenclature carbohydrate representation or in LINEARCODE® syntax, for linear code syntax principles see (Banin et al., Trends in Glycoscience and Glycotechnology, 14:127-37, 2002). A translation of the LINEARCODE® representation to IUPAC representation is presented in Table 1. All the glycan structures that discussed herein, unless mentioned otherwise, are connected in the indicated anomericity α or β to another molecular structure, linker, or solid phase.

In some embodiments, the reagents that are used to specifically bind and detect those anti glycans antibodies are the specific glycan structures. In other embodiments, the reagents are other molecules or macromolecules that include the specific glycan structure. The glycan or sugar structures can be only the a carbohydrate moiety (including monosaccharides an oligosaccharide or a polysaccharide) or displaying on any solid phase or other macromoleculeor any other molecular structure that includes the glycan. The glycan-containing structure can be naturally occurring, e.g., extracted from an organism, or synthetic.

For example, the anti-Glc(β1,3)Glc(β) antibody can be detected using the polysaccharide β-D(1,3) Glucan, a polymer of glucose units connected in a (β1,3) glycosidic bond. Thus, the glycan itself can be used for detecting the corresponding antibody or antibodies, as can any carbohydrate, peptide, protein, or any other molecular structure that includes the glycan.

In some embodiments, the reagents that are used to specifically bind and detect the anti glycans antibodies of the invention are peptides that mimic the carbohydrate antigens of the invention. The peptides can be used to identify specific anti glycan antibodies.

As used herein, the term "inflammatory bowel disease" is synonymous with "IBD" and is a collective term referring to both Crohn's disease and ulcerative colitis. Thus, an individual having either Crohn's disease or ulcerative colitis is defined herein as having IBD. Conversely, an individual having neither ulcerative colitis nor Crohn's disease does not have IBD as defined herein. The term "inflammatory bowel disease" distinguishes Crohn's disease and ulcerative colitis from all other disorders, syndromes or abnormalities of the gastroenterological tract including irritable bowel syndrome.

As used herein, the term "Non inflammatory bowel disease" is synonymous with "Non-IBD" and is a collective term referring to all other disorders, syndromes or abnormalities of the gastroenterological tract including irritable bowel syndrome (IBS).

The methods for diagnosing IBD may additionally include determining whether a sample is positive for anti-neutrophil cytoplasmic antibodies (ANCA). Anti-neutrophil cytoplasmic antibodies that produce a perinuclear staining pattern (pANCA) are elevated in 60-80% of UC patients and less frequently in CD and other disorders of the colon. Serum titers of ANCA are elevated in UC patients regardless of clinical status and, thus, do not reflect disease activity. High levels of serum ANCA also persist in UC patients five years post-colectomy. Although pANCA is found only very rarely in healthy adults and children, healthy relatives of UC patients have an increased frequency of pANCA, indicating that pANCA may be an immunogenetic susceptibility marker. ANCA reactivity is also present in a small portion of patients with Crohn's disease. The reported prevalence in CD varies, with most studies reporting that 10 to 30% of CD patients express ANCA (Saxon et al., J. Allergy Clin. Immunol. 86:202-210 (1990); Cambridge et al., Gut 33:668-674 (1992); Pool et al., Gut 3446-50 (1993); and Brokroelofs et al., Dig. Dis. Sci. 39:545-549 (1994)).

As used herein, the term "anti-neutrophil cytoplasmic antibody" is synonymous with "ANCA" and means antibodies to cytoplasmic components of a neutrophil. ANCA, such as serum or saliva ANCA, can be detected using an enzyme-linked immunosorbent assay with alcohol-fixed neutrophils. As disclosed herein, ANCA activity is divided into several broad categories: perinuclear to nuclear staining or cytoplasmic staining with perinuclear highlighting (pANCA); cytoplasmic neutrophil staining-without perinuclear highlighting (cANCA); and diffuse staining with speckling across the entire neutrophil (SAPPA). The term ANCA, as used herein, encompasses all varieties of anti-neutrophils cytoplasmic reactivity, including pANCA, cANCA and SAPPA. Similarly, the term "ANCA" encompasses all immunoglobulin isotypes including, for example, immunoglobulin A and G.

The determination of whether a sample is positive for ANCA using non-histological means is made using an antigen specific for ANCA using methods described in, e.g., U.S. Pat. No. 6,218,129. Such an antigen specific for ANCA can be, for example, whole fixed neutrophils; an unpurified or partially purified neutrophil extract; a purified UC pANCA antigen such as a purified protein, protein fragment or synthetically produced peptide; an anti-ANCA idiotypic antibody; or the like. Particularly useful antigens specific for ANCA are peptides, which can be chemically synthesized or expressed on the surface of phage. Purified antigens specific for ANCA can be, for example, histone H1, or an ANCA-reactive fragment of histone H1, as described in U.S. Pat. No. 6,074,835; an ulcerative colitis pANCA secretory vesicle antigen or an ANCA-reactive fragment thereof; or a microbial UC pANCA antigen, such as a histone H1-like antigen, porin antigen, Bacteroides antigen, or ANCA-reactive fragment thereof, as described in U.S. Pat. No. 6,033,864. One skilled in the art understands that additional antigens specific for ANCA, including antigenic fragments and ANCA-reactive peptides, can be identified, for example, using a representative UC pANCA monoclonal antibody.

Generating an Anti-glycan Antibody Profile

An anti-glycan antibody profile is generated using a sample obtained from the subject to be diagnosed. The term "sample," as used herein, means any biological specimen obtained from an individual that contains antibodies. A sample can be, for example, whole blood, plasma, saliva or other bodily fluid or tissue having antibodies, preferably a serum sample. In some embodiments, the sample is obtained surgically. In other embodiments, the sample is obtained non-surgically.

Samples can be diluted if desired before they are analyzed for anti-glycan antibodies. The subject can be, e.g., a human, a non-human primate (including a chimpanzee, ape, gorilla, old world primate), cow, horse, dog, cat, pig, goat, sheep, rodent (including, e.g., a mouse, rat, or guinea pig) Anti-glycan profiles can be determined by using methods known in the art for identifying antibodies to glycans. The methods include those disclosed in e.g., WO00/49412, or WO02/064556, or Schwarz et al., Glycobiology 13:749-54, 2003.

The methods are typically performed using reagents that specifically bind to the anti-glycan antibodies. The reagents can be, e.g., the specific glycan structures. Alternatively, the reagents can be other molecules or macromolecules that include the specific glycan structure. For example, the anti-Glc($\beta$1,3)Glc($\beta$) antibody can be detected using the polysaccharide $\beta$-D(1,3)Glucan, a polymer of glucose units connected in a ($\beta$1,3)glycosidic bond. Thus, the glycan itself can be used for detecting the corresponding antibody or antibodies, as can any carbohydrate, peptide, protein, or any other molecular structure that includes the glycan.

If desired, peptides that mimic carbohydrate antigens can be used in the methods and compositions described herein. The peptides can be used to identify specific anti glycan antibodies. Peptides which mimic structures recognized by antiglycan antibodies can be identified using methods known in the art, e.g., by screening a filamentous phage-displayed random peptide library (Zhan et al., Biochem Biophys Res Commun. 308:19-22, 2003; Hou et al., J Immunol. 17:4373-79, 2003).

Glycan antigens used to identify various anti-glycan antibodies can be obtained from a variety of other sources so long as the antigen is capable of binding specifically to the given anti-glycan Binding to anti-glycan antibodies can be performed using variety of other immunoassay for mats known in the art, including competitive and non-competitive immunoassay formats can also be used (Self and Cook, Curr. Opin. Biotechnol. 7:60-65 (1996), which is incorporated by reference). Other assays include immunoassays, such as enzyme-linked immunosorbent assays (ELISAs). An enzyme such as horseradish peroxidase (HRP), alkaline phosphatase (AP), $\beta$-galactosidase or urease can be linked to a secondary antibody selective for a primary anti-glycan antibody of interest. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a $\beta$-galactosidase detection system can be used with the chromogenic substrate o-nitrophenyl-a $\beta$-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab')$_2$ anti-human IgG-alkaline phosphatase, for example, can be purchased from Jackson Immuno-Research (West Grove, Pa.).

Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used (Rongen et al., J. Immunol. Methods 204:105-133 (1997)).

A radioimmunoassay can also be used for determining whether a sample is positive for a glycan antibody, or for determining the level of anti-glycan antibodies in a sample. A radioimmunoassay using, for example, an $^{125}$Iodine-labeled secondary antibody (Harlow and Lane, Antibodies A Laboratory Manual Cold Spring Harbor Laboratory: New York, 1988, which is incorporated herein by reference) is encompassed within the invention.

A secondary antibody may alternatively be labeled with a chemiluminescent marker. Such a chemiluminescent secondary antibody is convenient for sensitive, non-radioactive detection of anti-glycan antibodies and can be obtained commercially from various sources such as Amersham Lifesciences, Inc. (Arlington Heights, Ill.).

A detectable reagent may also be labeled with a fluorochrome. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of $^{125}$Iodine; or a fluorometer to detect fluorescence in the presence of light of a certain wavelength. For detection of enzyme-linked reagents, a quantitative analysis of the amount of anti-glycan antibodies can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Other methods include, e.g., flow cytometry (including bead based immunoassays), and phage display technology for expressing a recombinant antigen specific for an anti-glycan antibody. Phage particles expressing the antigen specific for a desired anti-glycan antibody can be anchored, if desired, to a multiwell plate using an antibody such as an anti phage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

Anti-glycan antibodies are conveniently detected by simultaneously analyzing multiple sample for the presence of one or more anti-glycan antibodies. For example, the antibodies can be detected using an array of reagents that can bind specifically to the anti glycan antibodies. Preferably, each reagent is provided in a different location with a defined address on the array. By exposing the sample to array all the anti glycan antibodies that bind to the reagent on the array can be detected in one test Suitable arrays that include reagents (preferably carbohydrate reagents) that specifically detect the CD-detecting antibodies disclosed herein, e.g., an anti-β-Glc( ) antibody, an anti-Glc(β1,4)Glc(β) antibody, an anti-Glc(β1,3)Glc(β) antibody, an anti-GlcNAc(β) 6-sulfate antibody, an anti-Man(α1,2)Man(α) antibody, an anti-Man(α1,3)Man(α) antibody, an anti-Man(α1,6)Man(α) antibody, an anti-Man (α) antibody, an anti-Man(α1,3)[Man(α1,6)]Man(α), an anti-Manna antibody, an anti-Dextran antibody, an anti-Xylan antibody, an anti-GlcNAc(β,1,4)GlcNAc(β) antibody, an anti-Gal 3-sulphate(β) antibody, an anti-aGlcNAc(β1,3)GalNAc(β) antibody, an anti-GlcNAc(β1,3)Gal(β1,4)Glc(β)antibody, an anti-α-Gal antibody, an anti-β-Gal antibody, an anti-α-GalNAc, an anti-α-Glc antibody, an anti-Gal(β1,6)Gal(β) antibody, an anti anti-GlcNAc(β1,6)GalNAc(α) or an anti-Gal(α1,3)Gal(β1,4)GlcNAc(β) antibody for diagnosing CD.

In some embodiments, the reagents that are used to specifically bind and detect those anti glycans antibodies are the specific glycan structures. In other embodiments, the reagents are other molecules or macromolecules that include the specific glycan structure. For example, the anti-Glc(β1,3)Glc(β) antibody can be detected using the polysaccharide β-D(1,3) Glucan, a polymer of glucose units connected in a (β1,3) glycosidic bond. Thus, the glycan itself can be used for detecting the corresponding antibody or antibodies, as can any carbohydrate, peptide, protein, or any other molecular structure that includes the glycan.

The array may additionally include a reagent or reagent, e.g., a carbohydrate reagent or reagents, that detect an anti-Mannan antibodies or a ANCA. In some embodiments, the glycans are attached to the array via a linker. A suitable linker includes at least one ethylene glycol derivative, at least two cyanuric chloride derivatives and an anilino group.

If desired, peptides that mimic carbohydrate antigens can be used in the methods and compositions described herein. The peptides can be used to identify specific anti glycan antibodies. Peptides which mimic structures recognized by antiglycan antibodies can be identified using methods known in the art, e.g., by screening a filamentous phage-displayed random peptide library (Zhan et al., Biochem Biophys Res Commun. 308:19-22, 2003; Hou et al., J Immunol. 17:4373-79, 2003.)

Interpreting Anti-glycan Antibody Binding Data

Typically, binding of anti-glycan antibodies to glycans in a sample is compared to a reference population, and differences in levels of the anti-glycan antibodies in the two samples are compared. The threshold for determining whether a test sample is scored positive for CD or APS, or Non-IBD based on its ant-glycan antibody profile can be altered depending on the sensitivity or specificity desired. The clinical parameters of sensitivity, specificity, negative predictive value, positive predictive value and overall agreement are calculated using true positives, false positives, false negatives and true negatives. A "true positive" sample is a sample positive for CD according to colonoscopy, radiologic and/or histologic analysis, which is also diagnosed positive according to a method of the invention. A "false positive" sample is a sample negative for CD by colonoscopic, radiologic and/or histologic analysis, which is diagnosed positive according to a method of the invention. Similarly, a "false negative" is a sample positive for CD by colonoscopic, radiologic and/or histologic analysis, which is diagnosed negative according to a method of the invention. A "true negative" is a sample negative for CD by colonoscopic, radiologic and/or histologic analysis, and also negative for CD according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of CD. Sensitivity is calculated as the number of true positive results divided by the sum of the true positives and false negatives. Sensitivity essentially is a measure of how well a method correctly identifies those with disease. In a method of the invention, the anti-glycan antibody values can be selected such that the sensitivity of diagnosing an individual is at least about 60%, and can be, for example, at least about 65%, 70%, 75%, 80%, 85%, 90% or 95%.

As used herein, the term "specificity" means the probability that a method is negative in the absence of CD. Specificity is calculated as the number of true negative results divided by the sum of the true negatives and false positives. Specificity essentially is a measure of how well a method excludes those who do not have CD. The anti-glycan cut-off value can be selected such that, when the sensitivity is at least about 70%, the specificity of diagnosing an individual is in the range of 30-60%, for example, 35-60%, 40-60%, 45-60% or 50-60%.

The term "positive predictive value," as used herein, is synonymous with "PPV" and means the probability that an individual diagnosed as having CD actually has the disease. Positive predictive value can be calculated as the number of true positives divided by the sum of the true positives and false positives. Positive predictive value is determined by the characteristics of the diagnostic method as well as the prevalence of the disease in the population analyzed. In a method of the invention, the anti-glycan antibody cut-off values can be selected such that the positive predictive value of the method in a population having a CD disease prevalence of 15% is at least about 5%, and can be, for example, at least about 8%, 10%, 15%, 20%, 25%, 30% or 40%.

As used herein, the term "overall agreement" means the accuracy with which a method diagnoses a disease state. Overall agreement is calculated as the sum of the true positives and true negatives divided by the total number of sample results and is affected by the prevalence of CD in the population analyzed. The anti-glycan antibody cut-off values can be selected such that the overall agreement of a method of the invention in a patient population having an CD disease prevalence of 15% is at least about 45%, and can be, for example, at least about 50%, 55% or 60%.

The invention will be illustrated in the following non-limiting examples.

EXAMPLE 1

Comparative Antiglycan Antibody Levels in the Serum of Crohn's Disease Patients and Patients with Other Digestive Diseases An anti-glycan antibody profile for IgG, IgA and IgM in the serum of the patients was obtained using GlycoChip® arrays (Glycominds, Ltd., Lod, Israel, Cat No. 9100). The arrays were constructed using procedures described in Schwarz et.al. Glycobiology, 13: 749-54, 2003. Anti-glycan antibody profiles of 45 CD patients and 27 patients with other digestive diseases were compared.

All serum samples were tested using GlycoChip® plates (Glycominds Ltd., Lod, Israel, Cat No. 9100), which was an array of mono and oligosaccharides covalently attached to a reduced volume 384-well micro titer plate. The mono and oligosaccharides displayed on the array are listed in Table 1. A translation of the LinearCode™ syntax used to describe glycan structure to IUPAC nomenclature can be found in Table 1.

The sera from patients volunteers who had signed an informed consent form were collected by Dr. Iris Dotan from the Gastroenterology and Liver Disease Institute in the Tel Aviv Sorasky Medical Center, Israel. All patients were diagnosed by Dr. Iris Dotan. The sera were collected in evacuated silicon coated gel containing tubes (Estar Technologies Cat#616603GLV). The sera were separated from the blood cells and kept frozen at −25° C. until use. The volume of all solutions added to the glycan array was 10 µl/well. The sera were diluted (1:20; saturating concentration) in 0.15M Tris-HCl pH 7.2, 0.085M Mg2SO4, 0.05% Tween 20 (TBST) containing 1% BSA (Sigma), dispensed into glycan array plates using a Tecan Genesis Workstation 200 automated handling system, and incubated for 60 min at 37° C. The plates were then washed with 250 µL/well Phosphate buffered Saline with 0.05% Tween 20 (PBST, Sigma) in an automatic plate washer (Tecan, POWERWASHER™). At this point the following reagents, diluted in TBST with 1% BSA, were added using a Multidrop 384 dispenser (Thermo Labsystems) and incubated for 60 min at 37° C.: for IgG, IgA, and IgM determination—the respective sub-class specific biotinylated goat anti-human Ig antibody (Jackson, Pa., USA) at 2.8 µg/ml, 3 µg/ml, and 0.9 µg/ml, respectively. Following washing with PBST, Streptavidin-conjugated europium (0.1 µg/ml) diluted in TBST with 1% BSA was added to each well followed by incubation for 30 min at 37° C. in the dark, and washing with PBST. DELFIA™ enhancement solution was then added to the wells and the plates were incubated for 30 to 45 min in the dark at room temperature. The fluorescence of the wells was read with a Victor 1420 (Wallac, Finland) plate reader using time resolved fluorescence settings of 340/612 nm (Excitation/Emission).

Some patients were tested for the presence of antibodies to perinuclear anti neutrophil cytoplasmic antibodies (pANCA) and anti-Saccharomyces cerevisiae (ASCA) IgG and IgA using a commercial kits made by INOVA, San-Diego, Calif. Cat. No 708290, 708865, 708870 respectively, according to the manufacturer instructions.

Tables 2, 3 and 4 present levels of IgG, IgA and IgM type antiglycan antibodies that were detected at significantly different levels between the CD patient population and the patient population with other digestive diseases. The values presented for IgG and IgA are absolute values. The values presented for IgM are absolute values after reduction of background. The back ground signal was measured as the signal received from wells with covalently bound p-nitrophenol. If the result was negative the signal was scored as zero.

Comparison of the average and median values of anti-carbohydrate antibodies in the CD and other digestive disease populations reveals a significant elevation in most of the anti glycans antibodies in the CD group as compared to the group containing individuals with the other digestive diseases group. None of the CD patients was found to be positive for pANCA antibodies. All the anti glycans levels that are displayed in Tables 2, 3 and 4 show statistically significant ($\alpha=0.05$; $p<0.05$) differences between the CD groups and the other digestive disease or normal group. Statistically significant differences between the medians of signals of CD and other digestive disease population and normal population were observed for antibodies bound to the following glycans: β-Glc, Glc(β1,4)Glc(β), Glc(β1,3)Glc(β), β-GlcNAc 6-sulfate, Man(α1,2)Man(α), Man(α1,3)Man(α), Man(α1,6)Man (α), Man(α), Man(α1,3)[Man(α1,6)]Man (α), Mannan, Dextran, Xylan, GlcNAc(β1,4)GlcNAc(β), Gal 3-sulphate(β), GlcNAc(β1,3)GalNAc(β), GlcNAc(β1,3)Gal(β,1,4)Glc(β), α-Gal,β-Gal,α-GalNAc,α-Glc, Gal(β1,6)Gal(β), GlcNAc (β1,6)GalNAc(α) and Gal(α1,3)Gal(β1,4)GlcNAc(β).

Table 5 shows the specificity and sensitivity of the different IgG anti glycans for differentiation between CD and other digestive diseases using different cut-off values. The cutoff values for each glycans where set as the $89^{th}$ percentile of the non CD group.

These results reveal a set of chemically defined glycan antigens that are useful for diagnosing CD. The levels of antibodies to those glycans are higher in the CD population than in the population of normal individuals or individuals with other digestive diseases. The antibodies that showed the greatest differentiation between CD and other digestive diseases in these studies are a set of antibodies to mannose based glycan fragment as well as antibodies to on β-Glc, Glc(β1,4)Glc(β), Glc(β1,3)Glc(β). Antibodies to Glc(β1,3)Glc(β), Man(α1,3)Man(α) and Man(α1,3)[Man (α1,6)]Man(α) were in particular able to differentiate between CD and other digestive disease at 57-62% sensitivity and 89%-93% specificity. The separation of those structures was better that what was achieved with Mannan (ASCA) 47% sensitivity and 89% specificity. Table 6 demonstrates that it is possible to use different cut of levels and to achieve higher sensitivity but lower specificity. Table 6 describe the sensitivity, specificity, True Positives (TP), True Negative (TN), False Positives (FP), and False Negatives (FN) and positive Predictive value (PPV) in different cut-of value for differentiation between CD and other digestive disease according to the level of anti Glc(β1,3)Glc(β), IgG and anti Mannan IgG. FIG. 1 is a Receiver Operator Characteristic (ROC) curve differentiating between individuals with CD and individuals with other digestive diseases according to levels of anti Glc(β1,3)Glc (β), IgG and anti Manna IgG antibodies.

By using combination of two or more glycans it is possible to improve the sensitivity with without reducing the specificity. For example, by setting cut-offs of 2000,000 for anti Glc(β1,3)Glc(β) and 2,400,000 for anti Mannan and setting the criteria for identification of CD as those individuals who are above cut-off levels for either of the antibodies it is possible to achieve 82% sensitivity with 70% specificity. Achieving this sensitivity by each of the antibodies alone would require lower cut off points, but these lower cutoffs would lead to poor specificity (e.g., a specificity of 37% for Glc(β, 1,3)Glc(β)).

EXAMPLE 2

Comparative Antiglycan Antibody Levels in the Serum of Crohn's Disease (CD) Colitis Patients and Ulcerative Colitis (UC) Patients An anti-glycan antibody profile for IgG and IgA in the serum of the patients was obtained using GlycoChip® arrays (Glycominds, Ltd., Lod, Israel, Cat No. 9100). The arrays were constructed using procedures described in Schwarz et. al., Glycobiology 13: 749-54, 2003. Anti-glycan antibody profiles of 6 CD colitis patients and 19 UC patients were compared. All serum samples were collected and tested as described in Example 1.

Figure 2A:
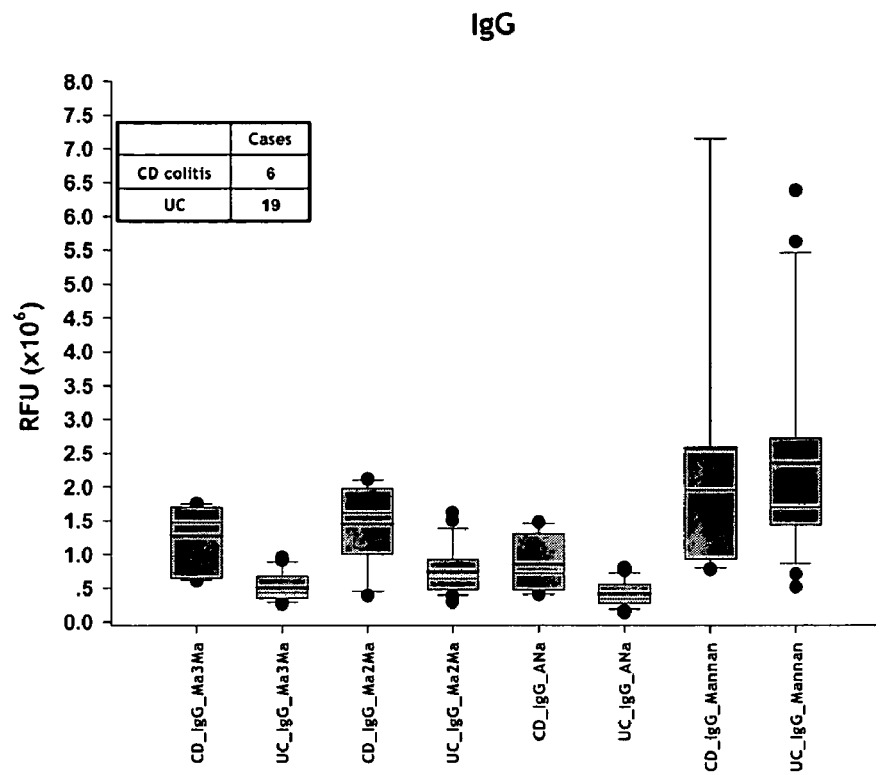
FIG. 2A is a box plot graph of the difference between CD colitis and UC groups for the levels of some antiglycan IgG antibodies.
Figure 2B:
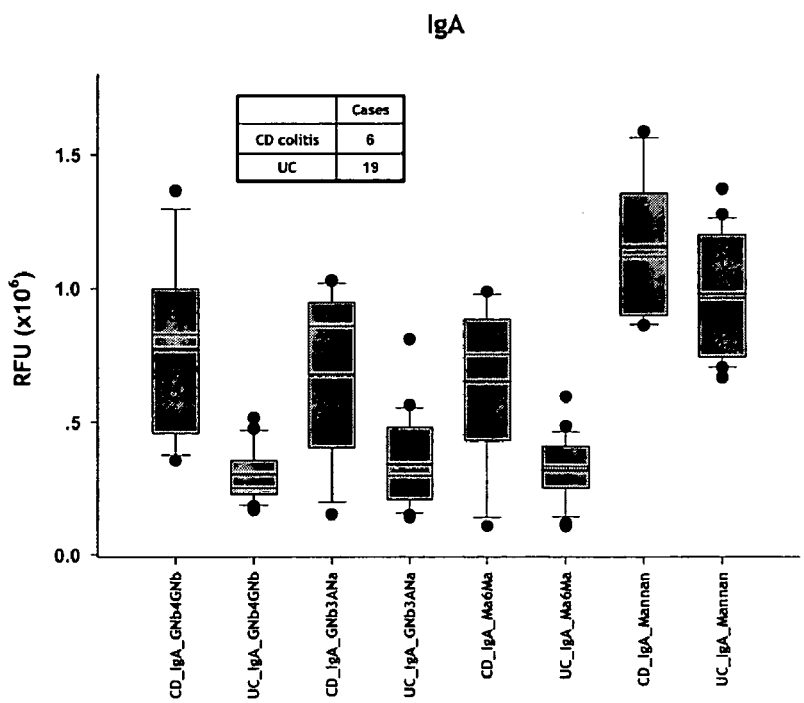
FIG. 2B is a box plot graph of the difference between CD colitis and UC groups for the levels of some antiglycan IgA antibodies.

Tables 7 and 8 show the levels of IgG and IgA type antiglycan antibodies that were detected at significantly different levels between the CD Colitis population and the UC population. The values presented for IgG and IgA are absolute values. Comparison of the average and median values of anti-carbohydrate antibodies in the CD Colitis patients and UC patients populations reveals a significant elevation in most of the anti glycans antibodies in the CD group as compared to the group containing individuals with the other digestive diseases group. All the anti glycans levels that are displayed in Tables 7 and 8 show statistically significant ($\alpha$=0.05; p<0.05) differences between the CD Colitis group and the UC group, with the exception of anti Mannan (ASCA) IgA and IgG. The most significant difference between the antibodies levels in the IgG class was found in the levels of anti Man(α1,3)Man(α), whereas for the IgA class the most significant difference was found between the levels of anti GlcNAc(β1,4)GlcNAc(β) antibodies. No statistically significant difference between the levels of anti Mannan (IgG or IgA) levels of the CD Colitis patients and UC patients populations was detected in these studies. FIG. 2 is a box plot graph of the difference between CD colitis and UC groups for the levels of some antiglycan IgG and IgA antibodies.

EXAMPLE 3

A Panel of Serological Antibodies (gASCA, ACCA, ALCA and AMCA) and CARD15 Gene Variations Predict a Complicated Disease Course and Need for Surgery in Some Crohn's Disease Patients A panel of anti glycan antibodies and CARD15 gene variants were examined to determine if they could improve predictions of a complicated disease course (penetrating, fistulizing or structuring, fibrostenosing disease course, or the need for surgery) in patients with Crohn's disease. Differentiation between patients with complicated disease outcomes and patients with non complicated disease outcomes (i.e., inflammatory type) facilitates selection of the must suitable treatment at an early stage of the disease.

Frozen samples from a total of 913 CD patients (mean age 42.3 years, 58% female) were retrospectively analyzed. Clinical characteristics for complications (strictures or fistulas) and the need for surgery were obtained. The samples were tested for gASCA, ACCA, ALCA, and AMCA by commercially available ELISA-assays (Glycominds Ltd, Israel) in a blinded manner. Briefly, mannan, and p-nitrophenyl derivatives of chitobioside, laminaribioside, and mannobioside (Man(α1,3)Man(α)) were covalently attached to the surface of a clear 96-well microtiter plate via a linker as previously described (Schwarz M et. al., Glycobiology. November 2003; 13(11):749-54.). Serum samples were diluted 1:100 in 1% BSA/TBST, pH 7.4, dispensed into the wells (50 μL per well) incubated for 30 min at 25° C., then washed with PBST buffer. Bound antibodies were labeled (30 min at 25° C.) with 50 μL of either horseradish peroxidase (HRP)-conjugated goat anti-human IgA (1:12000) for ACCA or IgG (1:25000) type-specific antibody for AMCA, ALCA and gASCA (both antibodies from Jackson, ImmunoResearch Laboratories, West Grove, Pa., USA), washed with PBST buffer, and 50 μL 3,3',5,5'-tetramethylbenzidine (TMB) was added for detection. The optical density (OD) at 595 nm was read after 15 min for ALCA gASCA and AMCA or 30 minutes for ACCA with a Victor 1420 plate reader (Wallac, Turku, Finland), the enzymatic reaction was stopped with 50 μL 1% sulfuric acid solution and read at 450 nm. Each plate includes a calibrator sample with a defined ELISA Unit (EU) value of 50 units. The final value of Units was calculated by dividing the OD of the test sample with the OD of the calibrator in the same plate and multiplying it by 50. All patients were genotyped for the main variants in CARD15 (R702W, G908R, 1007fs) as described in Vermiare et. al., Gastroenterology 123:106-11, 2002, and the number of CRAD15 variants (0-3) were recorded for each patient.

Statistical methods and data analysis: All antibodies data were transformed to square root to obtain a distribution as close as possible to normal. Student's T-test was used to assess significance differences in anti glycan antibodies between groups, and χ2 test was used for non-parametric variables. P-values of less than 0.05 were considered to be statistically significant. ROC curves were calculated using "Analyse-it" software package version 1.17. Regression analysis was performed using SPSS.

Predicting a Fistulizing or Fibrostenosing Disease Course in CD Patients

Significantly higher levels of all anti glycan antibodies (ALCA, ACCA, AMCA, gASCA, p<0.000001 for all) were detected in CD patients with complicated disease course (penetrating, fistulizing or structuring, fibrostenosing) as opposed to CD patients with inflammatory type of disease, see Table 9. The percentage of patients CARD15 variants in the group of CD patients with complicated disease course was higher than non complicated CD group (47.4% vs 34.8%, p=0.01).

Regression analysis considering all variables reveal that ALCA and ACCA are significant predictors as compared to gASCA and CARD15, see Table 10. Although AMCA levels antibodies were significantly higher in CD patients with complicated disease course AMCA did not contribute any additional significance.

The combined levels of ALCA, ACCA, gASCA and number of CARD15 variants, each multiplied by its regression coefficients to create a combined score, were determined. FIG. 3 describes ROC curves comparing the prediction performance of the known predictors gASCA and CARD15 to the combination of ALCA, ACCA, gASCA and number of CARD15. The area under the ROC curve for all markers combination is higher then for combination of gASCA and CARD15 (0.69 vs. 0.64).

Table 11 describes the diagnostic performance of combination of gASCA and CARD15, and the combination of ALCA, ACCA, gASCA and CARD15. It was found that both ALCA and ACCA significantly add to the prediction ability compared to the known ASCA and CARD15 variants. As can be seen in FIG. 3 and Table 11, the combined score identifies 45% of the CD who will have a complicated disease course with above 80% specificity. The combined markers offer clearly superior prediction ability compared the use of gASCA and CARD15 alone.

Predicting the Need for Surgery in CD Patients

Significantly higher levels of all anti glycan antibodies (ALCA, AMCA, p<0.01 and ACCA, gASCA, p<0.00001) were detected in CD patients needing surgery as opposed to CD patients who did not need surgery, see Table 12. The percentage of patients CARD15 variants in the group of CD patients needing surgery was higher than in the non-complicated CD group (46.0% vs 30.8%, p=0.001). Regression analysis considering all variables indicates that only ACCA is a significant predictor relative to the predictive ability of gASCA and CARD15, see Table 13. Although AMCA and ALCA levels antibodies were significantly higher in CD patients needing surgery, they did not add significant predictive ability over gASCA and CARD15.

The levels of ACCA, gASCA and the number of CARD15 variants, each multiplied by its regression coefficients, were added to create a combined score. Table 14 describes the diagnostic performance of combination of gASCA and CARD15, and the combination of ACCA, gASCA and CARD15.

These results demonstrate that ACCA significantly contributes to the prediction ability over the known ASCA and CARD15 variants. As can be seen in Table 14, the combined score identifies 30% of the CD patients with a need for surgery with above 90% specificity versus only 23% that can be identified if using only gASCA and CARD15. The combined performance are clearly better then the use of gASCA and CARD15 alone.

EXAMPLE 4

Improved Diagnosis of Inflammatory Bowel Disease (IBD) Using a Panel of Serological Antibodies (gASCA, ACCA, ALCA and AMCA) and CARD15 Gene Variations A panel of anti glycan antibodies and CARD15 gene variants were examined to determine if they could improve the diagnosis of IBD patients by differentiation between patients with IBD and OGD patients as well as normal population.

A total of 1225 IBD patients (913 CD, 272 UC, 40 IC), as well as 200 healthy controls and 113 patients with non-IBD gastrointestinal inflammation (diverticular disease) were tested for gASCA, ALGA, ACCA and AMCA by commercially available ELISA-assays (Glycominds Ltd, Israel) in a blinded manner. Briefly, mannan, and p-nitrophenyl derivatives of chitobioside, laminaribioside, and mannobioside were covalently attached to the surface of a clear 96-well microtiter plate via a linker as previously described (Scwharz et al., Glycobiology 13:749-54, 2003). Serum samples were diluted 1:100 in 1%BSA/TBST, pH 7.4, dispensed into the wells (50 µL per well) incubated for 30 mm at 25° C., then washed with PBST buffer. Bound antibodies were labeled (30 mm at 25° C.) with 50 µL of either horseradish peroxidase (HRP)-conjugated goat anti-human IgA (1:12000) for ACCA or IgG (1:25000) type-specific antibody for AMCA, ALGA and gASCA (both antibodies from Jackson, ImmunoResearch Laboratories, West Grove, Pa., USA), washed with PBST buffer, and 50 µL 3,3',5,5'-tetramethylbenzidine (TMB) was added for detection. The optical density (OD) at 595 nm was read after 15 mm for ALGA gASCA and AMCA or 30 minutes for ACCA with a Victor 1420 plate reader (Wallac, Turku, Finland). The enzymatic reaction was stopped with 50 µL 1% sulfuric acid solution and read at 450 nm. Each plate included a calibrator sample with a defined ELISA Unit (EU) value of 50 units. The final value of Units was calculated by dividing the OD of the test sample with the OD of the calibrator in the same plate and multiplying it by 50. All patients were genotyped for the main variants in CARD15 (R702W, G908R, 1007fs) as described in Vermiare et. al., Gastroenterology 123:106-11, 2002, and the number of CARD15 variants (0-3) were recoded for each patient.

Statistical methods and data analysis: All antibodies data were transformed to square root to get distribution as close as possible to normal. Student's T-test was used to assess significance differences in anti glycan antibodies between groups, P-values of less than 0.05 were considered to be statistically significant. ROC curves were calculated using "Analyse-it" software package version 1.17. Regression analysis was performed using SPSS.

Significantly higher levels of all anti glycan antibodies (ALCA, AMCA, gASCA, p<0.0001 for all) were observed in IBD patients as opposed to CD patients with inflammatory type of disease, see Table 15. Regression analysis considering all variables have shown that ALCA and AMCA are significant predictors over gASCA and CARD15, see Table 16.

A combined score was determined based on the levels of ALCA, ACCA, AMCA gASCA and number of CARD15 variants, each multiplied by its regression coefficients. FIG. 4 describes ROC curves comparing the diagnosis performance of the known predictors gASCA and CARD15 to the combination of ALCA, ACCA, gASCA and CARD15. The area under the ROC curve for all markers combination is higher then for combination of gASCA and CARD15 (0.830 vs. 0.765).

Table 17 describes the diagnostic performance of a combination of gASCA and CARD15, and the combination of ALCA, ACCA, AMCA, gASCA and CARD15. ALCA, ACCA and AMCA were found to significantly contribute to the prediction ability over the known ASCA and CARD15 variants. As can be seen in FIG. 4 and Table 17, the combined score identified IBD in 73% of subjects with above 80% specificity. The combined performance of ALCA, ACCA, gASCA, AMCA, and CARD15 were clearly superior than the use of gASCA and CARD15 alone.

EXAMPLE 5

Anti-laminarin IgG Antibodies Differentiate Between Crohn's Disease and Ulcerative Colitis or Irritable Bowel Syndrome and React in a Pattern that is Distinct from the Pattern Observed to ALCA Antibodies Anti-laminaribioside (Glc(β1,3)Glc(β)) carbohydrate antibody (ALCA) has been reported to be specific for CD patients, and to enable differentiation between CD and UC. Laminarin is storage polysaccharide of Laminaria and other brown algae; made up of (β1,3)-glucan with some (β1.6) linkages and branches. Here it is demonstrated that the reactivity of CD and UC patients towards anti-laminarin IgG and ALCA IgG are different. However, both can be used for differentiating between CD, and UC or IBS.

Frozen samples from CD (n=133), UC (n=75), and IBS (n=22) patients, diagnosed by standard clinical practice, were retrospectively analyzed. The samples were tested for anti-laminarin IgG antibodies using ELISA-assays. Briefly, laminarin (CAS Number 9008-22-4, Sigma L9634) and p-nitrophenyl derivative of Glc(β1,3)Glc(β) were covalently attached to the surface of a clear 96-well microtiter plate as previously described (Schwarz et al., Glycobiology 13:749-54, 2003). Serum samples were diluted 1:100 in 1% BSA/TBST, pH 7.4, dispensed into the wells (50 μL per well) incubated for 30 min at 25° C., then washed with PBST buffer. Bound antibodies were labeled (30 min at 25° C.) with 50 μL of either horseradish peroxidase (HRP)-conjugated goat anti-human IgG (1:25000) type-specific antibody (Jackson, ImmunoResearch Laboratories, West Grove, Pa., USA), washed with PBST buffer, and 50 μL 3,3',5,5'-tetramethylbenzidine (TMB) was added for detection. The optical density (OD) at 595 nm was read after 15 min with a Victor 1420 plate reader (Wallac, Turku, Finland), the enzymatic reaction was stopped with 50 μL 1% sulfuric acid solution and read at 450 nm. T-test was used to calculate significant difference between groups.

Significantly higher levels of anti-laminarin IgG were detected in CD patients vs UC, (p<0.001), and in CD vs IBS (p=0.01) see FIG. 5. Both ALCA and anti-laminarin differentiate between UC and CD patients. Using a Receiver Operator Characteristic (ROC) curve for differentiation between CD and UC (see FIG. 6), cut off values of 1.25 OD for anti-laminarin, and 0.57 OD for ALCA were chosen. This cutoff allowed for differentiation between CD and UC patients for anti-laminarin with 50.4% sensitivity, 90.7% specificity, 90.5% Positive predictive value, and 64.9% negative predictive value, and for ALCA, with 38.3% sensitivity, 90.7% specificity, 87.9% Positive predictive value, and 45.3% negative predictive value. FIG. 7 demonstrates that there is a subgroup of CD (n=25) and UC (n=5) patients that are negative for ALCA (below cutoff) but positive (above cut off) for anti-laminarin IgG antibodies. There is in addition a subgroup of CD (n=14) and UC (n=5) patients that are positive for ALCA (above cutoff) but negative (below cut off) for anti-laminarin IgG. Although laminaribioside and laminarin have common structural element in (Glc(β1,3)Glc(β)), laminarins nevertheless have a distinct structural fragments of (Glc(β1,6)Glc(β)) and Glc(β1,6)[Glc(β1,3)]Glc(β) branches. This reflects the different reactivities of CD and UC patients towards anti-laminarin IgG and ALCA IgG. However, (Glc(β1,6)Glc(β)), (Glc(β1,3)Glc(β)), Glc(β1,6)[Glc(β1,3)]Glc(β) or laminarin can be used for differentiating CD, and UC or IBS.

The descriptions given are intended to exemplify, but not limit, the scope of the invention. Additional embodiments are within the claims.

TABLE 1

Saccharides displayed on the glycan array

| Glycan No. | IUPAC | LINEAR-CODE® | Common Name |
|---|---|---|---|
| 0 | p-Nitrophenol | pNP-0 | |
| 1 | α-Gal | Aa | |
| 2 | β-Gal | Ab | |
| 3 | Gal(β1,3)GalNAc(α) | Ab3ANa | |
| 4 | Gal(β1,3)GlcNAc(β) | Ab3GNb | |
| 5 | Gal(β1,4)Glc(β) | Ab4Gb | Lactose |
| 6 | Gal(β1,6)Gal(β) | Ab6Ab | |
| 7 | α-GalNAc | ANa | |
| 8 | β-GalNAc | ANb | |
| 9 | α-Fuc | Fa | |
| 10 | β-Fuc | Fb | |
| 11 | α-Glc | Ga | |
| 12 | Glc(α1,4)Glc(α) | Ga4Ga | Maltose |
| 13 | Glc(α1,4)Glc(β) | Ga4Gb | |
| 14 | β-Glc | Gb | |
| 15 | Glc(β1,4)Glc(β) | Gb4Gb | Cellobiose |
| 16 | Glc(β1,4)Glc(β1,4)Glc(β) | Gb4Gb4Gb | Cellotriose |
| 17 | α-GlcNAc( ) | GNa | |
| 18 | β-GlcNAc | GNb | |
| 19 | GlcNAc(β1,3)GalNAc(α) | GNb3ANa | |
| 20 | GlcNAc(β1,4)GlcNAc(β) | GNb4GNb | Chitobiose |
| 21 | α-Rha | Ha | |
| 22 | β-GalA | Lb | |
| 23 | α-Man | Ma | |
| 24 | β-Man | Mb | |
| 25 | α-Neu5Ac | NNa | |
| 26 | α-L-Araf | Ra | |
| 27 | β-GlcA | Ub | |
| 28 | α-Xyl | Xa | |
| 29 | β-Xyl | Xb | |
| 30 | Gal(β1,3)[GlcNAc(β1,6)]GalNAc(α) | Ab3(GNb6)ANa | |
| 31 | Gal(β1,4)GlcNAc(α) | Ab4GNa | |
| 32 | Gal(α1,3)Gal(β1,4)GlcNAc(β) | Aa3Ab4GNb | Linear B-2 |
| 33 | Gal(β1,3)Gal(β1,4)GalNAc(β) | Ab4GNb | |
| 34 | Man(β1,4)GlcNAc(β) | Mb4Gb | |
| 35 | GlcNAc(β1,6)GalNAc(α) | GNb6ANa | |
| 36 | Fuc(α1,2)Gal(β) | Fa2Ab | |
| 37 | Man(α1,3)Man(α) | Ma3Ma | |
| 38 | β-GlcNAc 6-sulfate | GN[6S]b | |
| 39 | Glc(β1,3)Glc(β) | Gb3Gb | |
| 40 | β-Gal 3-sulfate | A[3S]b | |
| 41 | Man(α1,3)[Man(α1,6)]Man(β) | Ma3(Ma6)Mb | |
| 42 | GlcNAc(β1,3)Gal(α1,4)Glc(β) | GNb3Ab4Gb | Lacto-3 |
| 43 | Gal(α1,4)Gal(β1,4)Glc(β) | Aa4Ab4Gb | Pk antigen |
| 44 | Man(α1,6)Man(α) | Ma6Ma | |
| 45 | Man(α1,2)Man(α) | Ma2Ma | |
| 46 | Dextran | | Dextran |
| 47 | Mannam | | Mannam |
| 48 | Xylan | | Xylan |

TABLE 2

Fluorescent signals from binding of IgG antibodies to different glycans in CD patients and non CD patients. Glycans are presented in LINEARCODE ®.

| Patient No. | Clinical conditio | IgG Gb | IgG Gb3Gb | IgG Gb4Gb | IgG GN[6S]b | IgG Ma | IgG Ma3(Ma6)Mb | IgG Ma3Ma |
|---|---|---|---|---|---|---|---|---|
| 10,001 | Crohn's disease | 1,380,254 | 1,977,964 | 1,338,648 | 1,027,193 | 1,410,642 | 1,144,296 | 1,583,677 |
| 10,004 | Crohn's disease | 3,663,580 | 5,704,570 | 5,099,956 | 2,099,879 | 2,164,970 | 1,465,706 | 3,207,783 |
| 10,005 | Crohn's disease | 1,528,204 | 1,871,425 | 1,454,552 | 1,697,361 | 1,335,277 | 921,774 | 991,861 |
| 10,006 | Crohn's disease | 774,615 | 281,544 | 488,393 | 297,446 | 261,425 | 153,551 | 267,094 |
| 10,007 | Crohn's disease | 1,183,143 | 1,474,083 | 1,010,984 | 1,337,825 | 1,522,187 | 957,160 | 1,102,706 |
| 10,008 | Crohn's disease | 1,047,535 | 3,936,252 | 1,173,449 | 656,185 | 610,749 | 487,133 | 508,943 |
| 10,009 | Crohn's disease | 1,120,092 | 1,061,053 | 913,803 | 773,633 | 434,718 | 653,203 | 735,213 |
| 10,011 | Crohn's disease | 1,555,386 | 3,915,250 | 1,263,015 | 1,514,790 | 1,319,000 | 600,433 | 695,166 |
| 10,012 | Crohn's disease | 738,614 | 997,629 | 828,833 | 710,883 | 815,777 | 512,116 | 449,966 |
| 10,013 | Crohn's disease | 491,219 | 494,196 | 487,233 | 405,409 | 550,041 | 369,100 | 360,682 |
| 10,015 | Crohn's disease | 2,507,309 | 3,267,329 | 3,150,129 | 1,752,931 | 1,210,172 | 1,280,894 | 1,706,919 |
| 10,016 | Crohn's disease | 1,695,721 | 2,983,993 | 2,389,536 | 1,363,739 | 1,073,805 | 1,019,572 | 933,689 |
| 10,018 | Crohn's disease | 2,349,612 | 1,749,025 | 1,975,697 | 1,316,616 | 1,642,423 | 857,701 | 1,424,193 |
| 10,021 | Crohn's disease | 936,577 | 2,010,561 | 1,238,079 | 736,454 | 647,085 | 580,544 | 668,362 |
| 10,025 | Crohn's disease | 1,125,348 | 7,400,065 | 1,364,422 | 873,065 | 696,782 | 618,026 | 961,392 |
| 10,026 | Crohn's disease | 584,311 | 2,397,273 | 1,007,841 | 570,786 | 396,704 | 366,620 | 500,604 |
| 10,027 | Crohn's disease | 331,704 | 3,884,268 | 1,013,711 | 392,803 | 323,622 | 409,228 | 549,358 |
| 10,028 | Crohn's disease | 527,070 | 2,540,157 | 776,682 | 842,969 | 471,600 | 371,962 | 644,191 |
| 10,031 | Crohn's disease | 1,160,637 | 1,403,953 | 1,163,714 | 903,043 | 1,090,200 | 922,033 | 1,360,531 |
| 10,033 | Crohn's disease | 1,658,517 | 1,171,191 | 795,746 | 1,166,575 | 845,487 | 628,923 | 860,940 |
| 10,034 | Crohn's disease | 487,703 | 454,402 | 1,030,665 | 343,963 | 377,012 | 317,412 | 402,687 |
| 10,036 | Crohn's disease | 1,669,205 | 2,969,747 | 1,661,164 | 1,729,819 | 2,023,690 | 1,699,947 | 1,824,104 |
| 10,041 | Crohn's disease | 2,099,634 | 8,111,207 | 1,506,594 | 1,366,204 | 2,194,579 | 1,943,357 | 1,877,528 |
| 10,042 | Crohn's disease | 3,414,756 | 6,232,427 | 4,724,789 | 3,236,890 | 2,752,951 | 2,886,293 | 3,805,675 |
| 10,043 | Crohn's disease | 2,375,664 | 8,432,547 | 5,565,720 | 1,826,113 | 2,179,476 | 2,694,502 | 4,144,108 |
| 10,047 | Crohn's disease | 936,002 | 6,541,240 | 736,485 | 1,344,797 | 1,007,696 | 870,673 | 1,011,207 |
| 10,058 | Crohn's disease | 1,229,222 | 3,933,918 | 1,268,315 | 1,097,145 | 1,122,154 | 1,202,918 | 1,158,350 |
| 10,060 | Crohn's disease | 3,776,848 | 7,519,448 | 3,738,773 | 3,273,536 | 2,478,007 | 3,298,731 | 2,075,262 |
| 10,061 | Crohn's disease | 377,655 | 7,004,834 | 426,579 | 359,296 | 413,067 | 380,756 | 309,119 |
| 10,062 | Crohn's disease | 2,157,588 | 3,580,257 | 2,335,797 | 2,291,757 | 2,178,945 | 1,790,623 | 1,986,588 |
| 10,064 | Crohn's disease | 1,201,946 | 2,571,544 | 2,116,543 | 1,307,836 | 2,149,447 | 3,229,163 | 2,010,487 |
| 10,067 | Crohn's disease | 1,662,361 | 4,387,868 | 1,723,425 | 1,379,202 | 1,863,573 | 2,466,987 | 2,121,119 |
| 10,068 | Crohn's disease | 646,782 | 805,864 | 612,996 | 820,938 | 1,065,364 | 2,089,715 | 1,525,952 |
| 10,071 | Crohn's disease | 1,759,894 | 4,847,180 | 1,435,670 | 1,215,684 | 1,577,667 | 1,557,477 | 2,457,616 |
| 10,073 | Crohn's disease | 842,124 | 3,215,453 | 1,223,370 | 957,636 | 1,823,465 | 2,274,968 | 1,845,219 |
| 10,074 | Crohn's disease | 1,490,333 | 2,253,024 | 627,434 | 697,763 | 1,567,676 | 1,854,560 | 1,499,634 |
| 10,075 | Crohn's disease | 5,537,343 | 9,220,529 | 4,909,931 | 2,091,679 | 3,060,118 | 2,760,344 | 4,585,798 |
| 10,077 | Crohn's disease | 804,027 | 1,800,557 | 827,615 | 1,099,475 | 844,037 | 623,785 | 1,010,415 |
| 10,078 | Crohn's disease | 1,129,868 | 3,107,666 | 2,487,836 | 1,523,754 | 1,578,420 | 1,459,959 | 1,509,299 |
| 10,081 | Crohn's disease | 1,416,365 | 2,436,837 | 1,253,841 | 933,009 | 1,418,866 | 692,890 | 1,391,276 |
| 10,089 | Crohn's disease | 3,140,987 | 2,809,714 | 3,881,344 | 1,459,563 | 1,732,146 | 812,187 | 1,751,178 |
| 10,090 | Crohn's disease | 1,142,864 | 6,465,008 | 6,126,851 | 1,040,285 | 1,733,530 | 947,788 | 1,075,332 |
| 10,094 | Crohn's disease | 2,581,862 | 3,002,260 | 2,533,016 | 1,828,766 | 2,171,545 | 1,864,642 | 1,426,014 |
| 10,095 | Crohn's disease | 4,207,367 | 5,194,520 | 2,939,889 | 1,440,026 | 1,664,132 | 1,246,967 | 1,260,260 |
| 10,102 | Crohn's disease | 602,214 | 902,531 | 797,794 | 684,982 | 768,939 | 650,448 | 612,321 |
| 10,051 | No digestive disea | 2,345,273 | 2,322,503 | 1,994,931 | 2,743,406 | 1,185,818 | 1,041,917 | 1,987,733 |
| 10,052 | No digestive disea | 941,167 | 697,884 | 747,644 | 414,298 | 385,995 | 300,723 | 428,891 |
| 10,053 | No digestive disea | 346,709 | 531,417 | 276,989 | 339,655 | 283,955 | 275,260 | 326,337 |
| 10,054 | No digestive disea | 692,918 | 664,121 | 993,676 | 680,576 | 539,916 | 425,475 | 213,864 |
| 10,059 | Anal fissure | 931,210 | 1,033,766 | 686,670 | 585,045 | 482,405 | 434,125 | 288,509 |
| 10,066 | Proctitis/Psoriasis | 977,625 | 955,662 | 1,003,683 | 880,485 | 898,411 | 775,253 | 855,457 |
| 10,080 | No digestive disea | 1,742,919 | 2,061,316 | 1,679,459 | 882,024 | 678,925 | 529,711 | 671,004 |
| 10,082 | No digestive disea | 606,761 | 2,058,347 | 951,804 | 631,202 | 581,631 | 500,014 | 612,486 |
| 10,003 | Ulcerative colitis | 905,251 | 695,019 | 504,690 | 729,287 | 432,922 | 336,969 | 349,315 |
| 10,020 | Ulcerative colitis | 1,354,222 | 4,073,378 | 1,231,701 | 1,258,840 | 1,363,896 | 902,559 | 705,623 |
| 10,022 | Ulcerative colitis | 971,547 | 2,471,052 | 1,817,809 | 805,565 | 696,492 | 556,384 | 356,351 |
| 10,023 | Ulcerative colitis | 476,805 | 1,684,016 | 407,103 | 335,428 | 741,738 | 186,491 | 265,536 |
| 10,024 | Ulcerative colitis | 1,536,705 | 1,866,888 | 1,294,792 | 1,278,711 | 981,713 | 422,316 | 709,227 |
| 10,030 | Ulcerative colitis | 313,802 | 319,115 | 370,440 | 288,801 | 383,159 | 267,131 | 302,649 |
| 10,039 | Ulcerative colitis | 788,940 | 1,322,675 | 2,049,445 | 579,967 | 427,353 | 484,029 | 500,544 |
| 10,040 | Ulcerative colitis | 508,502 | 878,468 | 506,749 | 390,963 | 387,998 | 417,665 | 292,485 |
| 10,044 | Ulcerative colitis | 1,134,152 | 1,000,922 | 1,430,170 | 794,829 | 1,166,622 | 749,019 | 912,336 |
| 10,050 | Ulcerative colitis | 1,307,947 | 1,067,601 | 1,111,619 | 912,013 | 1,056,915 | 756,151 | 951,103 |
| 10,065 | Ulcerative colitis | 983,243 | 1,390,482 | 1,028,795 | 842,732 | 666,535 | 672,182 | 852,588 |
| 10,069 | Ulcerative colitis | 598,736 | 708,042 | 978,417 | 672,092 | 359,555 | 339,385 | 366,514 |
| 10,072 | Ulcerative colitis | 320,461 | 473,172 | 342,039 | 363,893 | 455,588 | 392,522 | 506,615 |
| 10,079 | Ulcerative colitis | 405,166 | 3,763,266 | 904,868 | 513,517 | 425,264 | 370,064 | 366,486 |
| 10,084 | Ulcerative colitis | 703,594 | 1,982,878 | 2,259,105 | 545,286 | 592,993 | 431,487 | 430,193 |
| 10,086 | Ulcerative colitis | 686,425 | 808,037 | 713,774 | 465,633 | 402,319 | 379,369 | 356,194 |
| 10,087 | Ulcerative colitis | 615,110 | 428,332 | 577,232 | 386,386 | 409,432 | 329,779 | 512,020 |
| 10,096 | Ulcerative colitis | 997,504 | 2,041,057 | 949,569 | 673,275 | 633,246 | 502,614 | 613,755 |
| 10,097 | Ulcerative colitis | 424,300 | 1,024,501 | 805,975 | 458,307 | 267,456 | 386,277 | 295,685 |

TABLE 2-continued

Fluorescent signals from binding of IgG antibodies to different glycans in CD patients and non CD patients. Glycans are presented in LINEARCODE ®.

| Patient No. | IgG Mannan | IgG Xylan | IgG Ma2Ma | IgG Aa | IgG Ab | IgG ANa | IgG Ga | IgG ASCA (IU) | pANC. |
|---|---|---|---|---|---|---|---|---|---|
| 10,001 | 7,628,072 | 5,577,215 | 849,550 | 1,026,505 | 820,014 | 466,637 | 1,258,316 | | |
| 10,004 | 7,476,981 | 4,596,345 | 3,150,106 | 1,843,625 | 1,861,915 | 1,134,167 | 2,304,370 | | |
| 10,005 | 5,827,429 | 4,982,760 | 857,537 | 1,060,156 | 1,075,287 | 1,097,821 | 1,936,815 | | |
| 10,006 | 1,310,353 | 543,373 | 496,362 | 161,595 | 114,468 | 135,241 | 302,565 | | |
| 10,007 | 3,891,170 | 2,264,442 | 894,460 | 1,206,075 | 1,032,927 | 804,835 | 1,442,191 | | |
| 10,008 | 7,900,531 | 2,858,992 | 918,954 | 1,143,656 | 1,918,663 | 330,682 | 2,831,482 | 80 | neg |
| 10,009 | 3,625,333 | 860,059 | 1,786,497 | 809,917 | 1,065,462 | 389,609 | 834,189 | | |
| 10,011 | 6,044,060 | 2,016,766 | 795,378 | 1,235,678 | 1,111,199 | 548,037 | 2,843,354 | | |
| 10,012 | 1,016,305 | 509,887 | 974,119 | 561,052 | 700,562 | 589,469 | 1,559,057 | | |
| 10,013 | 975,473 | 858,010 | 497,853 | 258,936 | 289,477 | 390,232 | 443,436 | | |
| 10,015 | 8,298,001 | 6,144,886 | 1,865,891 | 2,313,400 | 1,657,409 | 1,472,395 | 1,738,460 | | |
| 10,016 | 8,176,923 | 3,474,025 | 1,423,401 | 4,167,868 | 1,150,916 | 837,155 | 1,754,605 | | |
| 10,018 | 2,438,472 | 1,837,913 | 2,114,539 | 1,282,598 | 1,118,190 | 1,304,881 | 1,556,960 | | |
| 10,021 | 4,677,824 | 1,836,902 | 588,760 | 431,224 | 417,858 | 624,273 | 1,097,281 | | |
| 10,025 | 7,750,817 | 610,583 | 1,306,723 | 472,016 | 407,187 | 656,244 | 1,052,914 | 49 | neg |
| 10,026 | 4,427,669 | 409,875 | 754,569 | 814,529 | 5785940 | 804,015 | 794,465 | | |
| 10,027 | 4,184,500 | 1,477,393 | 409,405 | 1,011,607 | 325,270 | 225,780 | 860,654 | | |
| 10,028 | 1,133,383 | 580,308 | 388,120 | 400,412 | 374,748 | 565,621 | 933,864 | | |
| 10,031 | 6,070,889 | 5,267,773 | 1,024,636 | 614,602 | 545,633 | 434,719 | 1,029,243 | | |
| 10,033 | 8,668,310 | 1,372,493 | 999,469 | 487,495 | 699,125 | 710,940 | 1,311,185 | 108 | neg |
| 10,034 | 4,878,747 | 873,284 | 317,845 | 130,726 | 240,504 | 254,960 | 353,496 | | |
| 10,036 | 7,240,661 | 3,315,784 | 1,815,367 | 1,312,161 | 847,504 | 1,148,197 | 2,764,778 | | |
| 10,041 | 6,166,731 | 1,716,244 | 1,866,462 | 1,002,663 | 944,926 | 614,258 | 1,790,996 | | |
| 10,042 | 496,270 | 2,207,087 | 1,975,431 | 2,453,713 | 1,169,199 | 1,491,661 | 2,608,430 | | |
| 10,043 | 7,766,334 | 1,594,568 | 6,234,204 | 1,533,054 | 850,045 | 857,270 | 4,436,841 | | |
| 10,047 | 1,929,729 | 510,038 | 1,276,888 | 609,950 | 611,659 | 498,004 | 1,408,015 | | |
| 10,058 | 1,060,988 | 3,370,770 | 1,097,275 | 739,330 | 362,629 | 525,407 | 1,349,540 | 9 | neg |
| 10,060 | 6,622,444 | 2,830,021 | 2,587,250 | 2,051,391 | 1,446,321 | 1,320,361 | 3,268,250 | | |
| 10,061 | 1,440,898 | 277,672 | 1,125,410 | 264,741 | 171,160 | 196,852 | 711,761 | | |
| 10,062 | 5,928,994 | 4,135,199 | 1,725,643 | 1,300,507 | 939,781 | 1,000,803 | 1,809,051 | | |
| 10,064 | 7,015,353 | 4,157,443 | 1,546,371 | 3,778,662 | 695,314 | 536,893 | 1,212,355 | | |
| 10,067 | 4,103,563 | 1,406,894 | 3,016,091 | 1,374,889 | 342,454 | 509,166 | 2,469,775 | | |
| 10,068 | 856,925 | 520,606 | 1,364,558 | 236,510 | 358,229 | 468,415 | 1,037,834 | | |
| 10,071 | 5,460,883 | 3,745,128 | 1,980,052 | 1,109,196 | 1,555,029 | 698,647 | 1,691,995 | | |
| 10,073 | 7,159,301 | 6,675,699 | 2,240,331 | 421,833 | 391,254 | 494,614 | 1,551,800 | 72 | neg |
| 10,074 | 5,758,566 | 998,526 | 1,155,521 | 385,865 | 620,562 | 291,814 | 637,642 | 43 | neg |
| 10,075 | 7,712,384 | 6,780,460 | 4,835,416 | 1,560,441 | 1,816,357 | 994,508 | 2,812,624 | | |
| 10,077 | 1,238,077 | 908,558 | 726,513 | 1,221,596 | 352,019 | 371,924 | 1,047,431 | 15 | neg |
| 10,078 | 7,284,452 | 2,493,069 | 1,974,718 | 485,474 | 430,568 | 567,379 | 1,318,049 | 89 | neg |
| 10,081 | 5,617,906 | 4,927,776 | 1,038,228 | 799,172 | 688,062 | 440,608 | 759,311 | 39 | neg |
| 10,089 | 1,948,648 | 1,671,266 | 1,975,468 | 6,235,212 | 1,056,023 | 879,862 | 1,551,638 | 12 | neg |
| 10,090 | 7,029,051 | 1,226,773 | 966,138 | 616,608 | 527,011 | 612,911 | 1,024,901 | | |
| 10,094 | 3,755,208 | 1,359,423 | 1,889,334 | 503,455 | 449,558 | 730,609 | 1,321,795 | | |
| 10,095 | 5,473,997 | 1,284,127 | 1,587,782 | 704,930 | 541,730 | 441,276 | 2,730,801 | | |
| 10,102 | 779,631 | 515,705 | 999,742 | 425,568 | 257,965 | 402,233 | 1,119,216 | | |
| 10,051 | 3,590,967 | 1,737,022 | 1,601,098 | 325,091 | 277,928 | 291,398 | 765,670 | | |
| 10,052 | 736,762 | 776,440 | 345,938 | 791,714 | 924,915 | 549,282 | 3,092,123 | | |
| 10,053 | 792,256 | 625,138 | 314,716 | 226,043 | 634,923 | 193,841 | 1,110,574 | | |
| 10,054 | 1,280,390 | 1,600,067 | 484,686 | 194,929 | 147,713 | 136,850 | 665,259 | | |
| 10,059 | 2,858,138 | 725,949 | 411,652 | 491,103 | 482,992 | 344,004 | 798,813 | | |
| 10,066 | 1,721,699 | 1,307,196 | 878,148 | 532,501 | 611,229 | 555,691 | 889,848 | | |
| 10,080 | 1,953,921 | 1,987,675 | 556,509 | 544,141 | 349,525 | 358,554 | 729,190 | | |
| 10,082 | 4,193,860 | 1,440,782 | 616,439 | 736,553 | 722,306 | 386,966 | 1,006,756 | | |
| 10,003 | 1,022,364 | 504,020 | 640,303 | 187,886 | 165,987 | 257,702 | 659,133 | | |
| 10,020 | 2,556,960 | 1,911,575 | 641,831 | 1,107,251 | 1,087,519 | 758,804 | 1,269,501 | | |
| 10,022 | 5,619,844 | 2,466,668 | 689,170 | 612,362 | 645,057 | 377,726 | 1,467,537 | 40 | neg |
| 10,023 | 708,233 | 482,414 | 524,736 | 230,640 | 167,922 | 159,075 | 693,800 | | |
| 10,024 | 6,380,359 | 2,793,937 | 1,501,423 | 984,301 | 963,564 | 803,682 | 1,278,165 | | |
| 10,030 | 1,539,392 | 918,717 | 465,098 | 218,405 | 486,030 | 131,947 | 660,381 | | |
| 10,039 | 1,614,749 | 627,274 | 962,879 | 535,526 | 415,798 | 335,651 | 694,135 | | |
| 10,040 | 2,881,788 | 977,455 | 1,617,762 | 364,266 | 487,974 | 236,382 | 487,736 | | |
| 10,044 | 1,385,640 | 1,761,062 | 830,609 | 702,427 | 721,510 | 678,997 | 1,026,423 | | |
| 10,050 | 1,829,813 | 972,519 | 1,200,920 | 416,618 | 518,265 | 637,011 | 992,490 | | |
| 10,065 | 2,333,880 | 1,363,312 | 1,165,936 | 433,662 | 723,424 | 593,461 | 953,378 | | |
| 10,069 | 1,736,635 | 1,231,461 | 599,938 | 205,729 | 474,181 | 329,163 | 1,215,250 | 8 | neg |
| 10,072 | 3,309,525 | 471,592 | 482,991 | 192,896 | 198,520 | 231,397 | 1,015,614 | | |
| 10,079 | 1,665,869 | 576,365 | 293,343 | 150,330 | 173,270 | 460,674 | 983,715 | | |
| 10,084 | 1,655,824 | 548,041 | 509,662 | 438,643 | 376,558 | 448,064 | 735,412 | | |
| 10,086 | 2,174,929 | 1,547,265 | 476,815 | 203,077 | 107,695 | 323,692 | 877,230 | | |
| 10,087 | 1,319,329 | 382,061 | 380,169 | 254,434 | 239,993 | 338,760 | 578,501 | 5 | neg |
| 10,096 | 5,289,045 | 757,079 | 685,412 | 384,127 | 475,422 | 459,440 | 1,205,875 | | |
| 10,097 | 1,478,519 | 510,925 | 422,520 | 174,679 | 275,494 | 344,389 | 751,112 | | |

TABLE 2-continued

Fluorescent signals from binding of IgG antibodies to different glycans in CD patients and non CD patients. Glycans are presented in LINEARCODE ®.

Average

| | | | | | | | | |
|---|---|---|---|---|---|---|---|---|
| Crohn's disease | 1,625,556 | 3,518,257 | 1,898,152 | 1,239,749 | 1,345,981 | 1,243,023 | 1,426,441 | 4,904,849 |
| No Chrohn's Disea | 874,703 | 1,419,404 | 1,022,931 | 719,712 | 625,491 | 487,561 | 552,944 | 2,356,692 |

Median

| | | | | | | | | |
|---|---|---|---|---|---|---|---|---|
| Crohn's disease | 1,229,222 | 2,983,993 | 1,268,315 | 1,166,575 | 1,335,277 | 947,788 | 1,260,260 | 5,473,997 |
| No Chrohn's Disea | 788,940 | 1,033,766 | 961,804 | 631,202 | 539,916 | 425,475 | 438,891 | 1,736,635 |
| nest CD vs Non CD | 0.001630097 | 4.09721E−05 | 0.004132072 | 0.000688569 | 3.87726E−06 | 2.11271E−05 | 3.23203E−05 | 1.02024E−05 |

Average

| | | | | | | |
|---|---|---|---|---|---|---|
| Crohn's disease | 2,390,714 | 1,542,963 | 1,168,009 | 775,738 | 666,031 | 1,570,527 |
| No Chrohn's Disea | 1,148,297 | 714,840 | 431,083 | 476,137 | 397,133 | 985,319 |

Median

| | | | | | | |
|---|---|---|---|---|---|---|
| Crohn's disease | 1,716,244 | 1,276,888 | 814,529 | 688,082 | 589.469 | 1,349,540 |
| No Chrohn's Disea | 972,519 | 599,938 | 384,127 | 485,422 | 344,389 | 889,848 |
| nest CD vs Non CD | 0.00132903 | 0.000372938 | 0.00157261 | 0.00367082 | 0.000291031 | 0.001831333 |

TABLE 3

Fluorescent signals from binding of IgA and IgM antibodies to different glycans in CD patients and non CD patients. Glycans are presented in LINEARCODE ®.

| Patient No. | Clinical condition | IgA ASCA (IU) | IgA GNb3ANa | IgA GNb4GNb | IgA Ma6Ma | IgA Mannan | IgA Ab | IgA Ab6Ab | IgA GNb6ANa | IgA Aa3Ab4GNb3Ab4Gb |
|---|---|---|---|---|---|---|---|---|---|---|
| 10,001 | Crohn's disease | | 234,038 | 217,568 | 282,289 | 2,901,044 | 162,963 | 222,014 | 457,637 | 160,809 |
| 10,004 | Crohn's disease | | 756,739 | 769,776 | 665,102 | 8,412,607 | 336,469 | 723,124 | 704,572 | 312,718 |
| 10,005 | Crohn's disease | | 380,334 | 743,508 | 591,533 | 1,821,783 | 376,168 | 376,729 | 481,419 | 479,158 |
| 10,006 | Crohn's disease | | 255,036 | 243,466 | 308,555 | 1,177,812 | 181,747 | 301,883 | 397,318 | 147,591 |
| 10,007 | Crohn's disease | | 266,542 | 362,415 | 367,037 | 1,361,741 | 145,443 | 267,124 | 456,638 | 175,515 |
| 10,008 | Crohn's disease | | 674,715 | 769,785 | 779,172 | 2,027,609 | 357,896 | 656,873 | 690,791 | 405,779 |
| 10,009 | Crohn's disease | 33 | 649,639 | 641,504 | 669,799 | 1,044,123 | 531,803 | 459,344 | 760,867 | 505,990 |
| 10,011 | Crohn's disease | | 533,187 | 774,440 | 814,460 | 3,353,356 | 399,677 | 384,850 | 732,815 | 451,006 |
| 10,012 | Crohn's disease | | 448,590 | 617,530 | 434,796 | 927,252 | 793,281 | 351,295 | 733,115 | 258,768 |
| 10,013 | Crohn's disease | | 1,120,824 | 1,219,712 | 1,119,489 | 1,197,765 | 666,523 | 921,613 | 1,574,544 | 755,187 |
| 10,015 | Crohn's disease | | 973,774 | 1,365,559 | 988,046 | 1,585,774 | 671,617 | 644,176 | 1,884,674 | 823,921 |
| 10,016 | Crohn's disease | | 993,380 | 832,750 | 816,158 | 3,390,170 | 788,283 | 953,482 | 980,341 | 1,035,719 |
| 10,018 | Crohn's disease | | 872,212 | 826,559 | 884,411 | 1,355,268 | 905,785 | 944,644 | 1,114,615 | 1,120,640 |
| 10,021 | Crohn's disease | | 332,912 | 318,143 | 283,889 | 652,771 | 253,534 | 238,864 | 367,215 | 291,684 |
| 10,025 | Crohn's disease | 54 | 798,846 | 525,004 | 575,726 | 1,857,147 | 365,034 | 421,319 | 614,665 | 422,498 |
| 10,026 | Crohn's disease | | 752,315 | 660,677 | 693,119 | 887,797 | 341,464 | 350,620 | 1,150,207 | 365,731 |
| 10,027 | Crohn's disease | | 289,687 | 220,786 | 273,054 | 912,829 | 153,556 | 230,660 | 349,796 | 162,963 |
| 10,028 | Crohn's disease | | 153,168 | 355,502 | 107,442 | 861,641 | 54,145 | 99,647 | 194,085 | 70,783 |
| 10,031 | Crohn's disease | | 314,983 | 339,395 | 450,527 | 1,322,991 | 160,146 | 222,400 | 447,640 | 165,475 |
| 10,033 | Crohn's disease | 43 | 549,648 | 505,120 | 641,307 | 3,306,701 | 273,900 | 429,171 | 778,721 | 370,672 |
| 10,034 | Crohn's disease | | 245,321 | 299,225 | 183,931 | 1,010,743 | 171,098 | 122,238 | 369,875 | 243,404 |
| 10,036 | Crohn's disease | | 722,490 | 1,092,178 | 888,276 | 1,469,569 | 374,533 | 610,588 | 643,454 | 439,899 |
| 10,041 | Crohn's disease | | 342,492 | 461,173 | 317,150 | 1,410,747 | 199,838 | 291,742 | 205,720 | 181,180 |
| 10,042 | Crohn's disease | | 618,649 | 804,299 | 660,287 | 1,012,221 | 420,518 | 458,300 | 1,391,126 | 529,478 |
| 10,043 | Crohn's disease | | 1,052,988 | 1,108,655 | 790,738 | 2,747,555 | 605,571 | 542,596 | 569,482 | 628,435 |
| 10,047 | Crohn's disease | | 610,743 | 304,354 | 747,446 | 3,723,514 | 392,383 | 327,753 | 458,138 | 446,556 |
| 10,058 | Crohn's disease | 18 | 440,772 | 433,871 | 459,197 | 1,080,842 | 319,531 | 471,263 | 326,815 | 334,876 |
| 10,060 | Crohn's disease | | 979,671 | 655,668 | 2,481,088 | 5,456,752 | 644,454 | 689,063 | 709,019 | 664,299 |
| 10,061 | Crohn's disease | | 1,409,783 | 1,785,954 | 1,884,605 | 3,090,000 | 1,206,122 | 1,066,288 | 1,343,921 | 1,252,570 |
| 10,062 | Crohn's disease | | 973,871 | 1,265,139 | 1,048,774 | 7,127,363 | 1,022,422 | 795,474 | 886,127 | 648,731 |
| 10,064 | Crohn's disease | | 727,884 | 1,126,501 | 745,449 | 7,702,531 | 276,204 | 387,207 | 429,791 | 361,165 |
| 10,067 | Crohn's disease | | 241,286 | 289,944 | 334,231 | 1,120,597 | 212,729 | 275,459 | 299,711 | 163,918 |
| 10,068 | Crohn's disease | | 860,717 | 920,038 | 812,376 | 1,306,235 | 323,221 | 314,013 | 563,963 | 485,132 |
| 10,071 | Crohn's disease | | 1,047,039 | 798,301 | 995,826 | 2,852,441 | 641,204 | 545,489 | 738,740 | 619,438 |
| 10,073 | Crohn's disease | 113 | 1,181,172 | 1,345,794 | 844,175 | 5,292,942 | 947,978 | 502,913 | 549,025 | 1,734,370 |
| 10,074 | Crohn's disease | 18 | 620,845 | 648,591 | 563,327 | 3,405,349 | 457,812 | 527,719 | 487,532 | 484,359 |
| 10,075 | Crohn's disease | | 264,428 | 296,290 | 295,247 | 3,304,817 | 194,960 | 259,283 | 247,300 | 225,781 |
| 10,078 | Crohn's disease | 5 | 440,662 | 316,162 | 186,000 | 647,541 | 157,701 | 285,013 | 251,925 | 125,116 |
| 10,081 | Crohn's disease | 104 | 704,473 | 636,347 | 1,356,702 | 2,979,296 | 303,071 | 458,245 | 551,350 | 354,403 |
| 10,089 | Crohn's disease | 17 | 509,535 | 360,565 | 280,050 | 1,558,484 | 186,390 | 227,023 | 326,164 | 197,405 |
| 10,090 | Crohn's disease | 29 | 1,030,030 | 1,025,812 | 692,547 | 930,450 | 347,788 | 456,655 | 544,660 | 386,430 |
| 10,094 | Crohn's disease | | 405,004 | 376,014 | 275,862 | 3,304,817 | 412,253 | 337,503 | 306,485 | 305,576 |
| 10,095 | Crohn's disease | | 881,880 | 584,765 | 435,724 | 826,038 | 256,814 | 320,634 | 593,541 | 406,523 |
| 10,102 | Crohn's disease | | 38,087 | 41,257 | 14,441 | 540,612 | 45,568 | 78,182 | 27,736 | 37,539 |
| 10,095 | Crohn's disease | | 482,397 | 457,212 | 428,631 | 899,291 | 206,488 | 236,594 | 325,721 | 249,229 |
| 10,051 | No digestive disease | | 774,286 | 1,543,419 | 674,803 | 1,290,323 | 288,495 | 266,679 | 968,229 | 284,006 |

TABLE 3-continued

Fluorescent signals from binding of IgA and IgM antibodies to different glycans in CD patients and non CD patients. Glycans are presented in LINEARCODE ®.

| Patient No. | Clinical condition | IgA ASCA (IU) | IgA GNb3ANa | IgA GNb4GNb | IgA Ma6Ma | IgA Manan | IgA Ab | IgA Ab6Ab | IgA GNb6ANa | IgA Aa3Ab4GNb3Ab4Gb |
|---|---|---|---|---|---|---|---|---|---|---|
| 10,052 | No digestive disease | | 393,022 | 425,926 | 368,886 | 881,150 | 135,704 | 180,348 | 303,864 | 112,295 |
| 10,053 | No digestive disease | | 878,508 | 1,064,617 | 748,198 | 1,055,576 | 372,457 | 545,551 | 640,635 | 295,387 |
| 10,054 | No digestive disease | | 441,376 | 439,396 | 439,527 | 1,086,886 | 246,375 | 279,630 | 318,118 | 198,859 |
| 10,059 | Anal fissure | | 293,422 | 285,604 | 410,485 | 1,082,125 | 218,307 | 224,109 | 317,736 | 179,601 |
| 10,066 | Proctitis/Psoriasis | | 986,215 | 915,090 | 363,521 | 1,950,182 | 495,388 | 657,131 | 736,683 | 485,492 |
| 10,080 | No digestive disease | | 707,800 | 741,718 | 472,696 | 1,882,808 | 308,524 | 445,061 | 649,226 | 299,570 |
| 10,082 | No digestive disease | | 997,253 | 194,653 | 179,355 | 994,997 | 96,297 | 150,924 | 193,102 | 88,789 |
| 10,003 | Ulcerative colitis | | 150,201 | 168,212 | 117,909 | 941,586 | 76,240 | 128,755 | 143,652 | 78,004 |
| 10,020 | Ulcerative colitis | | 141,658 | 182,637 | 483,747 | 1,227,006 | 318,940 | 583,244 | 178,132 | 321,496 |
| 10,022 | Ulcerative colitis | 18 | 206,741 | 242,903 | 361,417 | 1,276,258 | 188,916 | 399,670 | 208,178 | 182,508 |
| 10,023 | Ulcerative colitis | | 533,213 | 250,089 | 229,484 | 963,955 | 118,896 | 136,478 | 201,303 | 131,550 |
| 10,024 | Ulcerative colitis | | 338,631 | 355,952 | 420,148 | 1,035,057 | 139,853 | 233,051 | 359,658 | 170,812 |
| 10,030 | Ulcerative colitis | | 206,757 | 302,015 | 432,372 | 1,372,125 | 127,271 | 136,718 | 323,945 | 126,499 |
| 10,039 | Ulcerative colitis | | 809,397 | 475,750 | 340,776 | 1,239,784 | 183,846 | 235,006 | 449,717 | 181,355 |
| 10,040 | Ulcerative colitis | | 169,128 | 226,449 | 177,048 | 1,052,267 | 113,511 | 176,403 | 249,464 | 117,935 |
| 10,044 | Ulcerative colitis | | 333,466 | 446,973 | 337,007 | 731,340 | 194,884 | 169,474 | 449,998 | 213,189 |
| 10,050 | Ulcerative colitis | | 293,205 | 249,396 | 280,097 | 665,569 | 239,071 | 305,609 | 324,797 | 312,988 |
| 10,065 | Ulcerative colitis | | 297,672 | 356,560 | 285,878 | 777,227 | 255,302 | 270,165 | 568,720 | 250,785 |
| 10,069 | Ulcerative colitis | 8 | 248,549 | 230,391 | 330,608 | 711,640 | 204,935 | 197,255 | 419,431 | 198,088 |
| 10,072 | Ulcerative colitis | | 263,715 | 210,346 | 256,584 | 1,240,896 | 286,381 | 174,449 | 263,180 | 169,568 |
| 10,079 | Ulcerative colitis | | 366,346 | 516,296 | 425,728 | 993,085 | 569,214 | 361,508 | 887,360 | 422,569 |
| 10,084 | Ulcerative colitis | | 203,365 | 235,662 | 248,564 | 702,479 | 442,837 | 206,449 | 182,069 | 254,076 |
| 10,086 | Ulcerative colitis | | 563,803 | 342,868 | 106,336 | 722,441 | 137,226 | 98,580 | 117,532 | 134,968 |
| 10,087 | Ulcerative colitis | 19 | 517,514 | 190,637 | 266,757 | 1,128,041 | 194,669 | 142,531 | 298,763 | 196,730 |
| 10,096 | Ulcerative colitis | | 536,802 | 460,213 | 594,745 | 910,216 | 398,374 | 513,371 | 588,895 | 405,529 |
| 10,097 | Ulcerative colitis | | 305,982 | 324,637 | 379,409 | 910,626 | 245,148 | 235,651 | 467,802 | 285,631 |
| | Average Crohn's disease | | 626,280 | 661,007 | 654,844 | 2,320,850 | 405,469 | 439,668 | 622,644 | 444,187 |
| | No Crohn's Disease | | 442,890 | 421,422 | 360,447 | 1,067,616 | 244,372 | 276,066 | 400,377 | 225,862 |
| | Median Crohn's disease | | 618,649 | 636,347 | 641,307 | 1,469,569 | 341,464 | 384,850 | 549,025 | 370,672 |
| | No Crohn's Disease | | 338,631 | 324,637 | 361,417 | 1,035,057 | 218,307 | 233,051 | 323,945 | 198,088 |
| | ttest CD vs Non CD | | 0.014066493 | 0.006955663 | 0.001158187 | 0.001111753 | 0.004639777 | 0.001853597 | 0.007398896 | 0.001413793 |

TABLE 4

Fluorescent signals from binding of IgM antibodies to different glycans in CD patients and non CD patients. Glycans are presented in LINEARCODE®.

| Patient No. | Clinical condition | IgM A[3S]b | IgM Aa | IgM Aa3Ab4GNb | IgM Aa4Ab4Gb | IgM Ab3(GNb6)ANa | IgM Ab3ANa | IgM GNb3Ab4Gb | IgM GNb3ANa | IgM Dextran | IgM Mannan |
|---|---|---|---|---|---|---|---|---|---|---|---|
| 10,001 | Crohn's disease | 0 | 0 | 0 | 0 | 0 | 0 | 608,457 | 657,592 | 230,160 | 2,084,216 |
| 10,004 | Crohn's disease | 0 | 0 | 0 | 0 | 0 | 0 | 542,436 | 730,879 | 360,390 | 722,969 |
| 10,005 | Crohn's disease | 0 | 68,568 | 0 | 0 | 0 | 0 | 1,375,070 | 2,933,445 | 388,048 | 117,931 |
| 10,006 | Crohn's disease | 0 | 0 | 0 | 402,561 | 161,405 | 0 | 1,695,894 | 1,963,416 | 3,110,617 | 810,502 |
| 10,007 | Crohn's disease | 0 | 0 | 0 | 0 | 166,017 | 0 | 1,178,646 | 993,402 | 969,884 | 612,220 |
| 10,008 | Crohn's disease | 0 | 0 | 0 | 0 | 0 | 0 | 735,201 | 1,372,932 | 468,089 | 796,727 |
| 10,009 | Crohn's disease | 0 | 0 | 0 | 0 | 0 | 0 | 322,451 | 680,970 | 59,317 | 0 |
| 10,011 | Crohn's disease | 0 | 0 | 0 | 0 | 0 | 0 | 205,150 | 1,039,057 | 494,848 | 0 |
| 10,012 | Crohn's disease | 0 | 0 | 0 | 0 | 0 | 0 | 972,528 | 1,688,071 | 1,221,314 | 1,490,590 |
| 10,013 | Crohn's disease | 1,274,136 | 1,194,898 | 1,392,444 | 0 | 0 | 0 | 1,174,565 | 2,419,276 | 2,049,830 | 2,588,785 |
| 10,015 | Crohn's disease | 387,307 | 390,644 | 325,647 | 0 | 0 | 0 | 1,054,492 | 1,545,327 | 2,107,182 | 1,418,006 |
| 10,016 | Crohn's disease | 260,897 | 0 | 14,251 | 0 | 0 | 0 | 1,328,058 | 3,127,245 | 1,667,531 | 70,238 |
| 10,018 | Crohn's disease | 248,996 | 228,314 | 158,547 | 0 | 0 | 0 | 1,430,548 | 1,912,812 | 2,166,938 | 1,971,045 |
| 10,021 | Crohn's disease | 762,735 | 852,490 | 700,041 | 0 | 327,738 | 4,353 | 1,469,658 | 2,142,999 | 2,094,545 | 1,285,376 |
| 10,025 | Crohn's disease | 466,121 | 319,573 | 565,269 | 0 | 0 | 0 | 2,975,994 | 3,777,466 | 2,312,303 | 2,435,341 |
| 10,026 | Crohn's disease | 0 | 0 | 0 | 0 | 0 | 0 | 745,061 | 3,384,432 | 3,509,606 | 409,591 |
| 10,027 | Crohn's disease | 151,387 | 437,186 | 547,822 | 0 | 0 | 0 | 1,779,829 | 3,425,917 | 1,720,479 | 3,144,625 |
| 10,028 | Crohn's disease | 510,204 | 540,836 | 723,234 | 0 | 81,777 | 46,618 | 1,562,488 | 2,857,289 | 2,236,531 | 3,049,138 |
| 10,031 | Crohn's disease | 165,011 | 242,183 | 199,166 | 0 | 16,958 | 0 | 578,140 | 849,394 | 973,540 | 910,393 |
| 10,033 | Crohn's disease | 14,440 | 0 | 1,113,845 | 0 | 0 | 0 | 879,981 | 1,786,910 | 822,422 | 587,545 |
| 10,034 | Crohn's disease | 770,101 | 695,338 | 641,641 | 0 | 121,757 | 78,717 | 1,117,458 | 1,646,989 | 1,616,572 | 1,320,077 |
| 10,036 | Crohn's disease | 163,646 | 642,487 | 2,180,044 | 0 | 0 | 0 | 2,573,605 | 2,518,175 | 2,570,459 | 1,552,108 |
| 10,041 | Crohn's disease | 123,889 | 89,104 | 151,581 | 0 | 0 | 0 | 781,745 | 1,733,620 | 929,763 | 1,789,860 |
| 10,042 | Crohn's disease | 0 | 1,345,482 | 1,158,234 | 0 | 0 | 0 | 2,298,533 | 3,652,328 | 4,851,471 | 1,342,805 |
| 10,043 | Crohn's disease | 0 | 0 | 0 | 0 | 0 | 0 | 943,254 | 3,801,228 | 349,534 | 628,039 |
| 10,047 | Crohn's disease | 831,510 | 857,115 | 1,076,947 | 0 | 465,551 | 147,112 | 1,854,934 | 3,495,774 | 3,233,236 | 1,936,982 |
| 10,058 | Crohn's disease | 128,555 | 220,493 | 428,347 | 0 | 0 | 0 | 897,206 | 1,775,488 | 766,028 | 983,376 |
| 10,060 | Crohn's disease | 363,862 | 1,284,367 | 474,206 | 0 | 19,714 | — | 926,098 | 2,910,549 | 1,296,914 | 859,571 |
| 10,061 | Crohn's disease | 690,511 | 1,095,509 | 1,128,863 | 0 | 621,675 | 149,877 | 2,612,378 | 3,589,958 | 2,379,098 | 4,685,631 |
| 10,062 | Crohn's disease | 715,200 | 1,485,943 | 2,464,680 | 0 | 220,921 | 188,832 | 1,464,405 | 2,716,333 | 1,256,919 | 1,245,680 |
| 10,064 | Crohn's disease | 245,487 | 664,556 | 1,633,864 | 0 | 635,144 | — | 1,893,522 | 3,343,233 | 2,212,175 | 2,923,034 |
| 10,067 | Crohn's disease | 222,329 | 141,266 | 75,592 | 0 | 0 | — | 631,443 | 1,765,852 | 1,280,499 | 1,011,954 |
| 10,068 | Crohn's disease | 0 | 0 | 0 | 0 | 0 | 0 | 0 | 829,715 | 0 | 0 |
| 10,071 | Crohn's disease | 67,858 | 77,830 | 88,393 | 0 | 272,031 | 0 | 669,203 | 1,023,200 | 302,307 | 2,573,082 |
| 10,073 | Crohn's disease | 0 | 0 | 147,447 | 30,339 | 184,079 | 5,781 | 693,896 | 1,180,873 | 1,506,812 | 2,148,575 |
| 10,074 | Crohn's disease | 0 | 0 | 0 | 0 | 0 | 0 | 1,549,121 | 2,082,886 | 1,386,468 | 531,246 |
| 10,075 | Crohn's disease | 65,267 | 34,147 | 241,365 | 0 | 65,722 | 0 | 839,403 | 1,814,627 | 1,571,440 | 582,384 |
| 10,077 | Crohn's disease | 0 | 214,916 | 88,848 | 0 | 321,513 | 0 | 576,897 | 1,309,189 | 1,059,111 | 359,244 |
| 10,078 | Crohn's disease | 0 | 0 | 0 | 0 | 0 | 0 | 43,955 | 952,620 | 464,210 | 791,441 |
| 10,081 | Crohn's disease | 0 | 0 | 0 | 0 | 0 | 0 | 28,385 | 907,289 | 0 | 93,410 |
| 10,089 | Crohn's disease | 0 | 0 | 0 | 0 | 0 | 0 | 0 | 319,608 | 309,448 | 0 |
| 10,090 | Crohn's disease | 0 | 0 | 0 | 0 | 6,781 | 0 | 326,922 | 551,737 | 253,387 | 635,071 |
| 10,094 | Crohn's disease | 68,166 | 118,072 | 97,315 | 93,394 | 70,477 | 4,567 | 427,222 | 634,599 | 741,918 | 1,331,605 |
| 10,095 | Crohn's disease | 0 | 0 | 0 | 0 | 0 | 0 | 331,811 | 1,357,109 | 711,417 | 2,803,494 |
| 10,102 | Crohn's disease | 0 | 0 | 0 | 0 | 0 | 0 | 0 | 78,782 | 0 | 860,022 |
| 10,051 | No digestive disease | 0 | 0 | 0 | 0 | 0 | 0 | 0 | 0 | 70,898 | 0 |

TABLE 4-continued

Fluorescent signals from binding of IgM antibodies to different glycans in CD patients and non CD patients. Glycans are presented in LINEARCODE ®.

| Patient No. | Clinical condition | IgM A[3S]b | IgM Aa | IgM Aa3Ab4GNb | IgM Aa4Ab4Gb | IgM Ab3(GNb6)ANa | IgM Ab3ANa | IgM GNb3Ab4Gb | IgM GNb3ANa | IgM Dextran | IgM Mannan |
|---|---|---|---|---|---|---|---|---|---|---|---|
| 10,052 | No digestive disease | 0 | 0 | 0 | 0 | 0 | 0 | 0 | 0 | 0 | 0 |
| 10,053 | No digestive disease | 0 | 803,031 | 314,948 | 0 | 0 | 0 | 909,819 | 1,957,899 | 2,693,514 | 160,549 |
| 10,054 | No digestive disease | 0 | 0 | 33,896 | 86,151 | 118,374 | 0 | 1,417,516 | 2,035,746 | 1,190,821 | 0 |
| 10,059 | Anal fissure | 0 | 0 | 0 | 47,680 | 0 | 0 | 621,074 | 880,869 | 553,501 | 0 |
| 10,066 | Proctitis/Psoriasis | 255,814 | 613,172 | 366,385 | 711,585 | 672,896 | 648,481 | 1,399,015 | 2,112,942 | 2,036,326 | 2,851,646 |
| 10,080 | No digestive disease | — | 142,813 | 1,437,670 | 357,136 | 255,635 | 13,016 | 682,951 | 1,753,399 | 466,998 | 226,598 |
| 10,082 | No digestive disease | — | — | — | 361,634 | 265,794 | 58,052 | 1,059,304 | 3,803,965 | 460,919 | — |
| 10,003 | Ulcerative colitis | — | — | — | — | — | — | — | — | — | — |
| 10,020 | Ulcerative colitis | 0 | 0 | — | — | — | — | — | — | — | — |
| 10,022 | Ulcerative colitis | 0 | 0 | 230,936 | 5,354 | 0 | 0 | 530,365 | 1,220,301 | 910,810 | 0 |
| 10,023 | Ulcerative colitis | 0 | 0 | 0 | 538,071 | 0 | 0 | 345,812 | 630,728 | 401,625 | 109,462 |
| 10,024 | Ulcerative colitis | 0 | 0 | 0 | 119,591 | 2,544,871 | 64,642 | 1,271,762 | 2,775,365 | 877,756 | 1,161,681 |
| 10,030 | Ulcerative colitis | 0 | 0 | 0 | 0 | 79,886 | 60,684 | 606,210 | 622,605 | 1,558,797 | 0 |
| 10,039 | Ulcerative colitis | 0 | 0 | 0 | 0 | 26,754 | 32,355 | 732,277 | 910,699 | 542,797 | 51,325 |
| 10,040 | Ulcerative colitis | 0 | 0 | 0 | 0 | 0 | 0 | 798,350 | 1,289,960 | 751,879 | 156,868 |
| 10,044 | Ulcerative colitis | 7,575 | 99,214 | 210,443 | 53,421 | 548,458 | 59,039 | 402,433 | 873,504 | 961,761 | 697,203 |
| 10,050 | Ulcerative colitis | 0 | 0 | 0 | 0 | 0 | 0 | 445,848 | 728,257 | 737,999 | 134,037 |
| 10,065 | Ulcerative colitis | 646,009 | 651,393 | 679,823 | 669,033 | 381,610 | 201,783 | 1,203,436 | 1,975,174 | 1,363,891 | 1,042,417 |
| 10,069 | Ulcerative colitis | 0 | 0 | 0 | 0 | 0 | 0 | 1,127,666 | 1,331,796 | 0 | 313,657 |
| 10,072 | Ulcerative colitis | 0 | 0 | 0 | 0 | 375,381 | 0 | 825,856 | 1,084,765 | 2,081,853 | 556,681 |
| 10,079 | Ulcerative colitis | 0 | 79,891 | 36,805 | 512,305 | 182,972 | 79,189 | 828,413 | 1,477,648 | 992,691 | 696,436 |
| 10,084 | Ulcerative colitis | 0 | 0 | 0 | 0 | 0 | 0 | 650,663 | 1,075,158 | 309,983 | 489,824 |
| 10,086 | Ulcerative colitis | 16,235 | 221,934 | 0 | 293,278 | 0 | 0 | 635,147 | 1,931,046 | 1,405,512 | 824,630 |
| 10,087 | Ulcerative colitis | 175,021 | 175,678 | 321,514 | 145,748 | 337,665 | 220,927 | 592,753 | 1,540,709 | 897,343 | 1,016,898 |
| 10,096 | Ulcerative colitis | — | — | — | — | — | — | 331,000 | 441,228 | 452,374 | 582,057 |
| 10,097 | Ulcerative colitis | — | — | — | — | 1,022,582 | 33,778 | 854,116 | 2,517,741 | 913,480 | 517,995 |
| | Average Crohn's disease | 193,725 | 294,251 | 395,947 | 11,695 | 83,517 | 13,908 | 1,024,356 | 1,895,124 | 1,333,594 | 1,277,643 |
| | No Crohn's Disease | 40,765 | 103,227 | 134,534 | 144,481 | 252,329 | 54,516 | 684,140 | 1,294,463 | 838,279 | 429,258 |
| | Median Crohn's disease | 14,440 | 68,568 | 88,848 | — | — | — | 897,206 | 1,765,852 | 1,221,314 | 983,376 |
| | No Crohn's Disease | — | — | — | — | — | — | 682,951 | 1,220,301 | 751,879 | 160,549 |
| | ttest CD vs Non CD | 0.014433781 | 0.036400697 | 0.041051138 | 0.000390828 | 0.047775166 | 0.059924749 | 0.029702213 | 0.017590683 | 0.034573847 | 0.000253081 |

TABLE 5

Specificity and sensitivity of the different IgG anti glycans for differentiation between CD and other digestive diseases using different cut-off values. The cutoff values for each glycans where set as the 89 percentiles of the other digestive disease group. Glycans are presented in LINEARCODE ®.

| Cut-off level | | Anti Glycan IgG antibodies | | | | | | | | | |
|---|---|---|---|---|---|---|---|---|---|---|---|
| | | Gb | Gb3Gb | Gb4Gb | GGN[6S]b | MMa | Ma3(Ma6)Mb | MMa3Ma | MMannan | XXylan | MMa2Ma |
| 65 percentile of non CD | Sensitivity for CD % | 76 | 73 | 62 | 62 | 58 | 60 | 71 | 78 | 58 | 71 |
| | Specificity for CD % | 70 | 63 | 67 | 70 | 67 | 78 | 70 | 67 | 63 | 67 |
| 75 percentile of non CD | Sensitivity for CD % | 62 | 71 | 58 | 60 | 71 | 60 | 64 | 73 | 62 | 71 |
| | Specificity for CD % | 74 | 74 | 78 | 78 | 52 | 78 | 78 | 74 | 74 | 78 |
| 85 percentile of non CD | Sensitivity for CD % | 56 | 64 | 51 | 49 | 49 | 56 | 62 | 67 | 40 | 62 |
| | Specificity for CD % | 81 | 81 | 81 | 81 | 85 | 85 | 81 | 81 | 81 | 85 |
| 90 percentile of non CD | Sensitivity for CD % | 49 | 62 | 33 | 42 | 44 | 56 | 60 | 47 | 36 | 40 |
| | Specificity for CD % | 89 | 89 | 89 | 89 | 89 | 93 | 89 | 89 | 89 | 89 |

TABLE 6

The sensitivity, specificity, True Positives (TP), True Negative (TN), False Positives (FP), and False Negatives (FN), and Positive Predictive Value (PPV) in different cut-of values for differentiation between CD and other digestive disease according to the level of Anti-Glc ($\beta$ 1,3) Glc ($\beta$) IgG.

| IgG Gb3Gb (abnormals above cut-off) | Sensitivity | Specificity | TP | TN | FP | FN | PPV |
|---|---|---|---|---|---|---|---|
| — | 100.0% | 0.0% | 45 | 0 | 27 | 0 | 62.5 |
| 0 | 95.6% | 0.0% | 43 | 0 | 27 | 2 | 61.43 |
| 6,963 | 95.6% | 3.7% | 43 | 1 | 26 | 2 | 62.32 |
| 27,235 | 93.3% | 3.7% | 42 | 1 | 26 | 3 | 61.76 |
| 27,402 | 91.1% | 3.7% | 41 | 1 | 26 | 4 | 61.19 |
| 62,662 | 88.9% | 3.7% | 40 | 1 | 26 | 5 | 60.61 |
| 78,554 | 88.9% | 7.4% | 40 | 2 | 25 | 5 | 61.54 |
| 86,949 | 88.9% | 11.1% | 40 | 3 | 24 | 5 | 62.5 |
| 87,267 | 86.7% | 11.1% | 39 | 3 | 24 | 6 | 61.9 |
| 108,535 | 86.7% | 14.8% | 39 | 4 | 23 | 6 | 62.9 |
| 133,683 | 86.7% | 18.5% | 39 | 5 | 22 | 6 | 63.93 |
| 156,547 | 86.7% | 22.2% | 39 | 6 | 21 | 6 | 65 |
| 174,695 | 86.7% | 25.9% | 39 | 7 | 20 | 6 | 66.1 |
| 241,622 | 84.4% | 25.9% | 38 | 7 | 20 | 7 | 65.52 |
| 242,565 | 84.4% | 29.6% | 38 | 8 | 19 | 7 | 66.67 |
| 312,940 | 84.4% | 33.3% | 38 | 9 | 18 | 7 | 67.86 |
| 317,476 | 84.4% | 37.0% | 38 | 10 | 17 | 7 | 69.09 |
| 344,750 | 82.2% | 37.0% | 37 | 10 | 17 | 8 | 68.52 |
| 371,507 | 80.0% | 37.0% | 36 | 10 | 17 | 9 | 67.92 |
| 371,648 | 80.0% | 40.7% | 36 | 11 | 16 | 9 | 69.23 |
| 378,722 | 77.8% | 40.7% | 35 | 11 | 16 | 10 | 68.63 |
| 379,003 | 77.8% | 44.4% | 35 | 12 | 15 | 10 | 70 |
| 430,129 | 77.8% | 48.1% | 35 | 13 | 14 | 10 | 71.43 |
| 441,239 | 77.8% | 51.9% | 35 | 14 | 13 | 10 | 72.92 |
| 454,736 | 75.6% | 51.9% | 34 | 14 | 13 | 11 | 72.34 |
| 489,733 | 75.6% | 55.6% | 34 | 15 | 12 | 11 | 73.91 |
| 525,203 | 73.3% | 55.6% | 33 | 15 | 12 | 12 | 73.33 |
| 526,443 | 73.3% | 59.3% | 33 | 16 | 11 | 12 | 75 |
| 546,432 | 73.3% | 63.0% | 33 | 17 | 10 | 12 | 76.74 |
| 612,367 | 73.3% | 66.7% | 33 | 18 | 9 | 12 | 78.57 |
| 851,962 | 73.3% | 70.4% | 33 | 19 | 8 | 12 | 80.49 |
| 979,509 | 71.1% | 70.4% | 32 | 19 | 8 | 13 | 80 |
| 1,209,892 | 71.1% | 74.1% | 32 | 20 | 7 | 13 | 82.05 |
| 1,266,954 | 71.1% | 77.8% | 32 | 21 | 6 | 13 | 84.21 |
| 1,317,083 | 68.9% | 77.8% | 31 | 21 | 6 | 14 | 83.78 |
| 1,376,957 | 66.7% | 77.8% | 30 | 21 | 6 | 15 | 83.33 |
| 1,379,223 | 66.7% | 81.5% | 30 | 22 | 5 | 15 | 85.71 |
| 1,425,185 | 64.4% | 81.5% | 29 | 22 | 5 | 16 | 85.29 |
| 1,461,919 | 64.4% | 85.2% | 29 | 23 | 4 | 16 | 87.88 |
| 1,560,904 | 62.2% | 85.2% | 28 | 23 | 4 | 17 | 87.5 |
| 1,574,353 | 62.2% | 88.9% | 28 | 24 | 3 | 17 | 90.32 |
| 1,705,604 | 60.0% | 88.9% | 27 | 24 | 3 | 18 | 90 |
| 1,722,429 | 57.8% | 88.9% | 26 | 24 | 3 | 19 | 89.66 |
| 1,732,725 | 57.8% | 92.6% | 26 | 25 | 2 | 19 | 92.86 |
| 1,817,947 | 55.6% | 92.6% | 25 | 25 | 2 | 20 | 92.59 |
| 1,825,768 | 53.3% | 92.6% | 24 | 25 | 2 | 21 | 92.31 |
| 1,869,774 | 51.1% | 92.6% | 23 | 25 | 2 | 22 | 92 |
| 1,880,984 | 48.9% | 92.6% | 22 | 25 | 2 | 23 | 91.67 |
| 1,994,899 | 46.7% | 92.6% | 21 | 25 | 2 | 24 | 91.3 |
| 2,067,775 | 44.4% | 92.6% | 20 | 25 | 2 | 25 | 90.91 |
| 2,154,175 | 42.2% | 92.6% | 19 | 25 | 2 | 26 | 90.48 |
| 2,324,221 | 40.0% | 92.6% | 18 | 25 | 2 | 27 | 90 |
| 2,467,429 | 37.8% | 92.6% | 17 | 25 | 2 | 28 | 89.47 |
| 2,551,776 | 35.6% | 92.6% | 16 | 25 | 2 | 29 | 88.89 |
| 2,703,085 | 35.6% | 96.3% | 16 | 26 | 1 | 29 | 94.12 |
| 2,850,072 | 33.3% | 96.3% | 15 | 26 | 1 | 30 | 93.75 |
| 3,096,078 | 31.1% | 96.3% | 14 | 26 | 1 | 31 | 93.33 |
| 3,186,273 | 28.9% | 96.3% | 13 | 26 | 1 | 32 | 92.86 |
| 3,441,678 | 28.9% | 100.0% | 13 | 27 | 0 | 32 | 100 |
| 3,511,076 | 26.7% | 100.0% | 12 | 27 | 0 | 33 | 100 |
| 3,559,430 | 24.4% | 100.0% | 11 | 27 | 0 | 34 | 100 |
| 3,578,889 | 22.2% | 100.0% | 10 | 27 | 0 | 35 | 100 |
| 4,137,076 | 20.0% | 100.0% | 9 | 27 | 0 | 36 | 100 |
| 4,327,530 | 17.8% | 100.0% | 8 | 27 | 0 | 37 | 100 |
| 5,107,549 | 15.6% | 100.0% | 7 | 27 | 0 | 38 | 100 |
| 5,545,432 | 13.3% | 100.0% | 6 | 27 | 0 | 39 | 100 |
| 5,640,050 | 11.1% | 100.0% | 5 | 27 | 0 | 40 | 100 |
| 5,724,798 | 8.9% | 100.0% | 4 | 27 | 0 | 41 | 100 |
| 6,708,583 | 6.7% | 100.0% | 3 | 27 | 0 | 42 | 100 |
| 6,891,638 | 4.4% | 100.0% | 2 | 27 | 0 | 43 | 100 |
| 7,209,245 | 2.2% | 100.0% | 1 | 27 | 0 | 44 | 100 |
| 7,299,442 | 0.0% | 100.0% | 0 | 27 | 0 | 45 | ##### |

TABLE 7

Fluorescent signals from binding of IgG antibodies to different glycans in CD Colitis patients and UC patients. Glycans are presented in LINEARCODE ®.

| Patient No. | Patient No. Clinical condition | IgG_Aa | IgG_Ab4GNa | IgG_Ab4GNb | IgG_Ana | IgG_Ga | IgG_Gb | IgG_GN(6S)b |
|---|---|---|---|---|---|---|---|---|
| 10015 | Crohn's disease | 2313399.5 | 635468 | 690377.5 | 1472394.5 | 1738460.25 | 2507309.25 | 1752931 |
| 10018 | Crohn's disease | 1282598 | 1535296.5 | 773145 | 1304881 | 1556959.75 | 2349611.5 | 1316616 |
| 10028 | Crohn's disease | 400412 | 2027543.5 | 276464.5 | 565620.5 | 933864 | 527070 | 842969 |
| 10068 | Crohn's disease | 236509.5 | 326480.5 | 365799.5 | 468415 | 1037833.75 | 646782.25 | 820937.5 |
| 10089 | Crohn's disease | 6235212 | 873746.5 | 828641.5 | 879861.5 | 1551637.75 | 3140987 | 1459563 |
| 10102 | Crohn's disease | 425568 | 1252680.5 | 275934.5 | 402232.5 | 1119215.5 | 602214.25 | 684982 |
| 10105 | Crohn's disease | | | | | | 208854.5 | |
| 10003 | Ulcerative colitis | 187885.5 | 377841 | 259127 | 257702 | 659132.75 | 905251.25 | 729287 |
| 10020 | Ulcerative colitis | 1107251 | 1374336.5 | 775070.5 | 758803.5 | 1269500.5 | 1354221.5 | 1258840 |
| 10022 | Ulcerative colitis | 612362 | 549887 | 517309 | 377725.5 | 1467537 | 971547.25 | 805564.5 |
| 10023 | Ulcerative colitis | 230639.5 | 287362 | 216928.5 | 159075 | 693799.5 | 476804.75 | 335428 |
| 10024 | Ulcerative colitis | 984300.5 | 860812.5 | 654889 | 803682 | 1278164.75 | 1536704.5 | 1278711 |
| 10030 | Ulcerative colitis | 218405 | 948666.5 | 148121.5 | 131947 | 660381 | 313801.5 | 288801 |
| 10039 | Ulcerative colitis | 535525.5 | 355678.5 | 308129 | 335650.5 | 694135 | 788940 | 579956.5 |
| 10040 | Ulcerative colitis | 364266 | 313945 | 301998.5 | 236382 | 487735.75 | 508502.25 | 390982.5 |
| 10044 | Ulcerative colitis | 702426.5 | 809831 | 486338 | 678997 | 1026423.25 | 1134152 | 794829 |
| 10050 | Ulcerative colitis | 416618 | 1388773 | 491837 | 637010.5 | 992490 | 1307946.75 | 912013 |
| 10065 | Ulcerative colitis | 433662 | 500898.5 | 456155 | 593461 | 953378.25 | 983242.75 | 842731.5 |
| 10069 | Ulcerative colitis | 205728.5 | 714726 | 259398.5 | 329163 | 1215249.5 | 598735.5 | 672092 |
| 10072 | Ulcerative colitis | 192896 | 194102.5 | 182286 | 231396.5 | 1015614.25 | 320461 | 363892.5 |
| 10079 | Ulcerative colitis | 150330 | 519316 | 199636 | 460673.5 | 983715.25 | 405166 | 513526.5 |
| 10084 | Ulcerative colitis | 438643 | 696196 | 312418 | 448064 | 735412.25 | 703594 | 545286 |
| 10086 | Ulcerative colitis | 203076.5 | 203979 | 127167.5 | 323691.5 | 877230.25 | 686424.75 | 465633 |
| 10087 | Ulcerative colitis | 254433.5 | 421656 | 304673.5 | 338759.5 | 578500.5 | 615110 | 386385.5 |
| 10096 | Ulcerative colitis | 384127 | 1044393 | 244746 | 459440 | 1205875.25 | 997504 | 673275 |
| 10097 | Ulcerative colitis | 174679 | 267596.5 | 167481.5 | 344388.5 | 751111.75 | 424300.25 | 458307 |
| 10029 | Ulcerative colitis | | | | | | 1024750 | |
| Average | Crohn's disease colitis | 1,815,617 | 1,108,536 | 535.060 | 848,901 | 1,322,995 | 1,628,996 | 1,146,333 |
| | Ulcerative colitis | 410,382 | 622,631 | 337,564 | 416,106 | 923,441 | 791,179 | 647,134 |
| Med | Crohn's disease colitis | 854,083 | 1,063,214 | 528,089 | 722,741 | 1,335,427 | 1,498,197 | 1,079,793 |
| | Ulcerative colitis | 364,266 | 519,316 | 301,999 | 344,389 | 953,378 | 703,594 | 579,957 |
| | ttest | 0.012022185 | 0.026037602 | 0.044509262 | 0.002568067 | 0.006995736 | 0.009487981 | 0.003042923 |

| Patient No. | Patient No. Clinical conditon | IgG_GNb | IgG_GNb6ANa | IgG_Ma | IgG_Ma2Ma | IgG_Ma3(Ma6)Mb | IgG_Ma3Ma | IgG_Mannan |
|---|---|---|---|---|---|---|---|---|
| 10015 | Crohn's disease | 2155136.5 | 2105251 | 1210171.5 | 1865891 | 1280893.5 | 1706919 | 8298001.25 |
| 10018 | Crohn's disease | 1853996.5 | 1063920.5 | 1642422.5 | 2114538.5 | 857700.5 | 1424193 | 2438472 |
| 10028 | Crohn's disease | 815951 | 1646003 | 471600 | 388120 | 371961.5 | 644719 | 1133383.25 |
| 10068 | Crohn's disease | 995101.5 | 1045720 | 1065364 | 1364558 | 2089715 | 1525952 | 856924.5 |
| 10089 | Crohn's disease | 6756773.5 | 2984861.5 | 1732145.5 | 1975468 | 812187 | 1751178 | 1948648.25 |
| 10102 | Crohn's disease | 984931 | 788111 | 768939 | 999741.5 | 650448 | 612321 | 779630.5 |
| 10105 | Crohn's disease | | | | | | | 2577209 |
| 10003 | Ulcerative colitis | 575919 | 821537.5 | 432922 | 640303 | 336989 | 349314.5 | 1022364.25 |
| 10020 | Ulcerative colitis | 1372903 | 1524422.5 | 1363896 | 641830.5 | 902559 | 706622.5 | 2556959.5 |
| 10022 | Ulcerative colitis | 892125 | 2107553 | 696491.5 | 689169.5 | 556384 | 356351 | 5619843.5 |
| 10023 | Ulcerative colitis | 380898.5 | 412904.5 | 741737.5 | 524735.5 | 185491 | 265536 | 708232.5 |
| 10024 | Ulcerative colitis | 1293243.5 | 1428660.5 | 981713 | 1501423 | 422316 | 709226.5 | 6380358.5 |
| 10030 | Ulcerative colitis | 368437.5 | 1521634 | 383159 | 465097.5 | 267131 | 302649 | 1539392 |
| 10039 | Ulcerative colitis | 603719 | 900021.5 | 427352.5 | 962878.5 | 484028.5 | 500544 | 1614748.75 |
| 10040 | Ulcerative colitis | 943099.5 | 1502139 | 387998 | 1617762 | 471664.5 | 292485 | 2881787.75 |
| 10044 | Ulcerative colitis | 1069004 | 740744 | 1166622 | 830608.5 | 749019 | 912334.5 | 1385639.5 |
| 10050 | Ulcerative colitis | 1120248 | 836121 | 1056914.5 | 1200920 | 756150.5 | 951103 | 1829812.5 |
| 10065 | Ulcerative colitis | 2518317 | 610962.5 | 666534.5 | 1165935.5 | 672182 | 852588 | 2333879.75 |
| 10069 | Ulcerative colitis | 899127 | 584783.5 | 359555 | 599937.5 | 339385 | 366514 | 1736634.75 |
| 10072 | Ulcerative colitis | 423833 | 310437.5 | 455587.5 | 482990.5 | 392522 | 506615 | 3309524.75 |
| 10079 | Ulcerative colitis | 508108 | 411685.5 | 425263.5 | 293342.5 | 370064 | 356484.5 | 1665868.75 |
| 10084 | Ulcerative colitis | 826299.5 | 552446.5 | 592992.5 | 509651.5 | 431486.5 | 430193 | 1655823.75 |
| 10086 | Ulcerative colitis | 744875 | 321304 | 402319 | 476814.5 | 379368.5 | 356194 | 2174928.5 |
| 10087 | Ulcerative colitis | 353199 | 256942.5 | 409432 | 380168.5 | 329778.5 | 512019.5 | 1319329 |
| 10096 | Ulcerative colitis | 910091.5 | 558828.5 | 633246 | 685412 | 502613.5 | 613755 | 5289044.5 |
| 10097 | Ulcerative colitis | 1859201.5 | 433687 | 267456 | 422519.5 | 386277 | 295685 | 1478518.5 |
| 10029 | Ulcerative colitis | | | | | | | 512254 |
| Average | Crohn's disease colitis | 2,260,315 | 1,605,645 | 1,148440 | 1,451,386 | 1,010,484 | 1,277,459 | 2,575,843 |
| | Ulcerative colitis | 929,613 | 833,526 | 623,747 | 741,658 | 467,443 | 507,117 | 2,447,510 |
| Med | Crohn's disease colitis | 1,424,549 | 1,354,962 | 1,137,768 | 1,615,225 | 834,944 | 1,475,073 | 1,541,016 |
| | Ulcerative colitis | 892,125 | 610,963 | 455,588 | 640,303 | 417,665 | 430,193 | 1,736,635 |
| | ttest | 0.022705775 | 0.012278151 | 0.004574538 | 0.003038408 | 0.001689271 | 2.23605E-05 | 0.88985599 |

TABLE 8

Fluorescent signals from binding of IgA antibodies to different glycans in CD Colitis patients and UC patients. Glycans are presented in LINEARCODE®.

| Patient No. | Clinical condition | IgA_Gb3Gb | IgA_Aa3Ab4GNb3Ab4Gb | IgA_GNb | IgA_Aa4Ab4Gb | IgA_Ab | IgA_Ab3(GNb6)ANa | IgA_Ab3GNb | IgA_Ab6Ab | IgA_ANa | IgA_ANb | IgA_Gb |
|---|---|---|---|---|---|---|---|---|---|---|---|---|
| 10015 | Crohn's disease | 3792249.5 | 823920.5 | 1848069.5 | 642431 | 671617 | 582327.5 | 1250743.5 | 644176 | 712552.5 | 782432 | 2352257.5 |
| 10018 | Crohn's disease | 1050178.5 | 1120640 | 1108481.5 | 692655.5 | 905785 | 806576 | 555300 | 944644 | 509272.5 | 534881 | 1744966.5 |
| 10028 | Crohn's disease | | 70782.5 | | 65409 | 54145 | 50555 | 64293 | 99647 | 102094.5 | 100331.5 | 193866.5 |
| 10068 | Crohn's disease | | 485132 | | 423765 | 323220.5 | 300755 | 278180.5 | 314013 | 335295 | 303011.5 | 1012507 |
| 10089 | Crohn's disease | | 386429.5 | | 475156 | 347788 | 300281.5 | 396131 | 456654.5 | 426221.5 | 420382.5 | 993118 |
| 10102 | Crohn's disease | | 249229 | | 289752.5 | 206488 | 157775.5 | 189939 | 236594 | 224709.5 | 254464 | 625656 |
| 10105 | Crohn's disease | | | | | | | | | | | |
| 10003 | Ulcerative colitis | | 78003.5 | | 74646.5 | 76239.5 | 77832.5 | 76386 | 128755 | 99557 | 98065.5 | 143964 |
| 10020 | Ulcerative colitis | | 321496 | | 286915 | 319939.5 | 316325 | 358795.5 | 583244 | 550607 | 531219.5 | 748577 |
| 10022 | Ulcerative colitis | | 182507.5 | | 253611.5 | 188916 | 269222.5 | 230976.5 | 399670 | 278082.5 | 323070.5 | 676825 |
| 10023 | Ulcerative colitis | | 131549.5 | | 113203.5 | 118895.5 | 106896 | 121660.5 | 136477.5 | 183293.5 | 145928.5 | 314442 |
| 10024 | Ulcerative colitis | | 170812 | | 191188.5 | 139852.5 | 313233 | 141818.5 | 233050.5 | 146876 | 189008.5 | 832661.5 |
| 10030 | Ulcerative colitis | | 126498.5 | | 114379.5 | 127270.5 | 101520.5 | 93169.5 | 136717.5 | 136593.5 | 231126 | 409200 |
| 10039 | Ulcerative colitis | | 181355 | | 168185 | 183845.5 | 185994.5 | 165022.5 | 235006 | 180943 | 168373 | 491547 |
| 10040 | Ulcerative colitis | | 117934.5 | | 122886.5 | 113510.5 | 116982.5 | 110072.5 | 176402.5 | 148789 | 177785.5 | 279361 |
| 10044 | Ulcerative colitis | | 213188.5 | | 235379.5 | 194883.5 | 299006 | 282039.5 | 169473.5 | 153085.5 | 161501 | 753256 |
| 10050 | Ulcerative colitis | | 312988 | | 253641 | 239070.5 | 233244.5 | 213519.5 | 305608.5 | 264615.5 | 271901 | 695130 |
| 10065 | Ulcerative colitis | | 250784.5 | | 555877.5 | 255301.5 | 267297.5 | 174792 | 270164.5 | 251877.5 | 203122.5 | 697130.5 |
| 10069 | Ulcerative colitis | | 198087.5 | | 171640.5 | 204934.5 | 161723.5 | 230896.5 | 197254.5 | 183682 | 212249.5 | 635934 |
| 10072 | Ulcerative colitis | | 169567.5 | | 230948 | 286381 | 174653 | 174006 | 174449 | 167844 | 185039.5 | 365880.5 |
| 10079 | Ulcerative colitis | | 422569 | | 430651.5 | 569214 | 337161 | 328102 | 361507.5 | 352796.5 | 366925 | 554240.5 |
| 10084 | Ulcerative colitis | | 254076 | | 234589 | 442836.5 | 212473 | 202150.5 | 206448.5 | 192001 | 206100.5 | 581235.5 |
| 10086 | Ulcerative colitis | | 134968 | | 117207 | 137226 | 73241.5 | 78799.5 | 98580 | 67717 | 101404 | 197886.5 |
| 10087 | Ulcerative colitis | | 196730 | | 404271.5 | 194668.5 | 134105.5 | 164685 | 142530.5 | 145004 | 171203 | 483024 |
| 10096 | Ulcerative colitis | | 405,528.5 | | 392063.5 | 398373.5 | 352667 | 365977.5 | 513370.5 | 391423 | 433166 | 869958.5 |
| 10097 | Ulcerative colitis | | 285630.5 | | 280728 | 245147.5 | 193135 | 199541 | 235651 | 203575.5 | 229678 | 553467 |
| 10029 | Ulcerative colitis | | | | | | | | | | | |
| Average Crohns | | | 522,689 | | 431,528 | 418,174 | 366,378 | 455,765 | 449,288 | 385,024 | 399,250 | 1,153,729 |
| UC | | | 218,646 | | 243,790 | 233,500 | 206,669 | 195,390 | 247,598 | 215,703 | 231,940 | 541,248 |
| Med Crohns | | | 435,781 | | 449,461 | 335,504 | 300,518 | 337,156 | 385,334 | 380,758 | 361,697 | 1,002,813 |
| UC | | | 196,730 | | 234,589 | 194,884 | 193,135 | 174,792 | 206,449 | 183,294 | 203,123 | 554,241 |
| ttest | | | 0.003432508 | | 0.017087855 | 0.042789261 | 0.036632153 | 0.015545789 | 0.028930448 | 0.018529045 | 0.024586727 | 0.003969787 |

| Patient No. | Clinical condition | IgA_GNb3Ab4Gb | IgA_GNb3Ana | IgA_GNb4GNb | IgA_GNb6ANa | IgA_Ma | IgA_Ma2Ma | IgA_Ma3(Ma6)Mb |
|---|---|---|---|---|---|---|---|---|
| 10015 | Crohn's disease | 957892.25 | 973773.5 | 1365558.5 | 1884673.5 | 793071.5 | 3415595 | 746825.5 |
| 10018 | Crohn's disease | 809108 | 872211.5 | 826559 | 1114615 | 961742.5 | 2917815.5 | 727784 |

TABLE 8-continued

Fluorescent signals from binding of IgA antibodies to different glycans in CD Colitis patients and UC patients. Glycans are presented in LINEARCODE®.

| 10028 | Crohn's disease | 186673.5 | 226701.5 | 144574 | 153168.25 | 355502 | 194085 | 94336.5 | 256032 | 87390 |
|---|---|---|---|---|---|---|---|---|---|---|
| 10068 | Crohn's disease | 628503 | 691170.5 | 1218454 | 860716.75 | 920038.25 | 563962.5 | 524544 | 807816.5 | 435971 |
| 10089 | Crohn's disease | 140344.5 | 975042.5 | 2982001.5 | 1030029.75 | 1025812.25 | 544660 | 556490 | 819048.5 | 379526.5 |
| 10102 | Crohn's disease | 628931.5 | 317767 | 288563.75 | 482396.5 | 457211.75 | 325721 | 261633.5 | 729964 | 231998.5 |
| 10105 | Crohn's disease | | | 313559 | 376495 | 459207.5 | | | | |
| 10003 | Ulcerative colitis | 141554.5 | 200912.5 | 116158.75 | 150200.75 | 168212.25 | 143651.5 | 115658.5 | 287171.5 | 95305 |
| 10020 | Ulcerative colitis | 786919.5 | 923043.5 | 146937.5 | 141658 | 182637 | 178131.5 | 256154 | 1079174.5 | 192167 |
| 10022 | Ulcerative colitis | 455035 | 491029.5 | 218443.5 | 206741 | 242902.75 | 208178 | 324237.5 | 656144 | 211938 |
| 10023 | Ulcerative colitis | 284436.5 | 275060.5 | 238630.25 | 533213 | 250089 | 201303 | 227006.5 | 637593 | 207601.5 |
| 10024 | Ulcerative colitis | 442657 | 479785.5 | 288009 | 338630.5 | 355951.5 | 359657.5 | 338794 | 1125587.5 | 262327 |
| 10030 | Ulcerative colitis | 284786.5 | 408023.5 | 236756.5 | 206756.5 | 302015 | 323944.5 | 272317.5 | 856355.5 | 201701 |
| 10039 | Ulcerative colitis | 517175.5 | 392005 | 786417 | 809396.5 | 475749.5 | 449716.5 | 387887.5 | 710761 | 276315.5 |
| 10040 | Ulcerativecolitis | 218811.5 | 280689.5 | 205950.75 | 169128.25 | 226448.5 | 249464 | 164073.5 | 312896.5 | 135720 |
| 10044 | Ulcerative colitis | 473594.5 | 555971 | 392169.25 | 334466.25 | 446973.25 | 449997.5 | 326666.5 | 748596 | 239592.5 |
| 10050 | Ulcerative colitis | 382399.5 | 526927.5 | 383543.5 | 293205.25 | 249395.5 | 324796.5 | 314891.5 | 547079 | 281154 |
| 10065 | Ulcerative colitis | 670787.5 | 457057 | 291427.75 | 297671.75 | 356560.25 | 568719.5 | 316328.5 | 847658 | 287586.5 |
| 10069 | Ulcerative colitis | 527218.5 | 363936.5 | 194509.5 | 248548.5 | 230391 | 419430.5 | 389266 | 724998.5 | 354004 |
| 10072 | Ulcerative colitis | 357007 | 390922.5 | 288597 | 263714.5 | 210346.25 | 263180 | 229358.5 | 817809 | 179841 |
| 10079 | Ulcerative colitis | 2254719.5 | 1048892.5 | 406795.25 | 366346 | 516296.25 | 887360 | 514181.5 | 1012361 | 612803 |
| 10084 | Ulcerative colitis | 434302.5 | 414222 | 179011.25 | 203365.25 | 235661.5 | 182069 | 194750.5 | 1041362.5 | 178116 |
| 10086 | Ulcerative colitis | 207273 | 193242 | 433317.5 | 563802.75 | 342868 | 117532 | 95669.5 | 191239 | 121532 |
| 10087 | Ulcerative colitis | 475046 | 343527 | 203492.5 | 517514 | 190636.5 | 298763 | 303731 | 700059.5 | 248842.5 |
| 10096 | Ulcerative colitis | 824120.5 | 833330.5 | 445703.25 | 536801.5 | 460213 | 588895 | 564102 | 1394898 | 522042.5 |
| 10097 | Ulcerative colitis | 738068.5 | 484123 | 299604.5 | 305982.25 | 324637 | 467802 | 289141 | 737150 | 276116 |
| 10029 | Ulcerative colitis | | | | | | | | | |
| Average Crohns | | 1,281,530 | 861,205 | 1,066,766 | 728,716 | 825,114 | 771,286 | 531,970 | 1,491,045 | 434,916 |
| UC | | 551,506 | 477,300 | 302,913 | 341,376 | 303,578 | 351,715 | 296,011 | 759,415 | 257,090 |
| Med Crohns | | 839,555 | 833,107 | 883,500 | 866,464 | 873,299 | 554,311 | 540,517 | 813,433 | 407,749 |
| UC | | 455,035 | 414,222 | 288,009 | 297,672 | 250,089 | 323,945 | 303,731 | 737,150 | 239,593 |
| ttest | | 0.04289942 | 0.02591308 | 0.003184372 | 0.001126656 | 1.02649E-05 | 0.014389095 | 0.0113452 | 0.029286279 | 0.032460361 |

| Patient No. | Clinical condition | IgA_Ma3Ma | IgA_Ma6Ma | IgA_Mb | IgA_Xa | IgA_Xb | IgA_Mannan |
|---|---|---|---|---|---|---|---|
| 10015 | Crohn's disease | 999203.5 | 988046 | 1137247 | 792398.5 | 989360 | 1585773.5 |
| 10018 | Crohn's disease | 717096 | 884411 | 1436105 | 818794.5 | 701470 | 1355267.5 |
| 10028 | Crohn's disease | 103552 | 107441.5 | 107648 | 142920 | 83003.5 | 861640.5 |
| 10068 | Crohn's disease | 503945.5 | 812375.5 | 752123.5 | 678194 | 705638.5 | 1306234.5 |
| 10089 | Crohn's disease | 459454 | 692546.5 | 1278177.5 | 674436 | 787323.5 | 930450 |
| 10102 | Crohn's disease | 316389 | 428631 | 433463 | 387340.5 | 392556 | 899290.5 |
| 10105 | Crohn's disease | | | | | | |
| 10003 | Ulcerative colitis | 105407.5 | 117909 | 175959.5 | 155615 | 153281.5 | 941585.5 |

TABLE 8-continued

Fluorescent signals from binding of IgA antibodies to different glycans in CD Colitis patients and UC patients. Glycans are presented in LINEARCODE®.

| | | | | | | | |
|---|---|---|---|---|---|---|---|
| 10020 | Ulcerative colitis | 234420 | 483746.5 | 511744 | 833230 | 813730 | 1227005.5 |
| 10022 | Ulcerative colitis | 215720.5 | 361416.5 | 494957.5 | 501185 | 616145 | 1276257.5 |
| 10023 | Ulcerative colitis | 240763.5 | 229483.5 | 248143 | 288172 | 261699.5 | 963954.5 |
| 10024 | Ulcerative colitis | 295575.5 | 420147.5 | 595161.5 | 517119.5 | 493560.5 | 1035056.5 |
| 10030 | Ulcerative colitis | 229526.5 | 432372 | 321790.5 | 320339.5 | 301633 | 1372125 |
| 10039 | Ulcerative colitis | 280618 | 340776 | 503526 | 392243 | 502137 | 1239784 |
| 10040 | Ulcerative colitis | 121149.5 | 177048 | 234442 | 270652 | 238040.5 | 1052266.5 |
| 10044 | Ulcerative colitis | 308066 | 337006.5 | 434514 | 215294.5 | 231719.5 | 731340 |
| 10050 | Ulcerative colitis | 196723 | 280097 | 275211.5 | 285774 | 234435 | 665568.5 |
| 10065 | Ulcerative colitis | 286285.5 | 285877.5 | 421455 | 346017.5 | 268919 | 777226.5 |
| 10069 | Ulcerative colitis | 439389 | 330608 | 378909.5 | 415744 | 300095.5 | 711639.5 |
| 10072 | Ulcerative colitis | 253729.5 | 256584 | 848373.5 | 241471.5 | 238841 | 1240896 |
| 10079 | Ulcerative colitis | 859776.5 | 425728 | 618248 | 513057 | 575291 | 993084.5 |
| 10084 | Ulcerative colitis | 217626 | 248563.5 | 316798.5 | 287812 | 311632 | 702478.5 |
| 10086 | Ulcerative colitis | 100620.5 | 106336 | 185590.5 | 101801.5 | 98237.5 | 722440.5 |
| 10087 | Ulcerative colitis | 264208.5 | 266756.5 | 331533 | 270612.5 | 263230 | 1128040.5 |
| 10096 | Ulcerative colitis | 499770 | 594745 | 1301964 | 613521.5 | 539601 | 910216 |
| 10097 | Ulcerative colitis | 236299 | 379409 | 431939.5 | 331780 | 311639.5 | 910626 |
| 10029 | Ulcerative colitis | | | | | | |
| Average | Crohns | 516,607 | 652,242 | 857,461 | 582,347 | 609,892 | 1,156,443 |
| | UC | 283,457 | 319,716 | 454,224 | 368,497 | 355,467 | 979,031 |
| Med | Crohns | 481,700 | 752,461 | 944,685 | 676,315 | 703,554 | 1,118,342 |
| | UC | 240,764 | 330,608 | 421,455 | 320,340 | 300,096 | 963,955 |
| | ttest | 0.026205708 | 0.000976406 | 0.01751963 | 0.027583859 | 0.021610873 | 0.131187019 |

TABLE 9

Anti-glycan antibody levels in CD patients with complicated disease (fistulizing or fibrostensoing) versus CD patients with non complicated disease (inflammatory).

| Antibodies | Anti glycan antibodies levels, $(EU)^{0.5}$ Mean (SD) | |
|---|---|---|
| | Complicated disease (n = 264) | Non complicated disease (n = 474) |
| ALCA | 6.6 (2.0)** | 5.8 (2.0) |
| ACCA | 7.8 (3.4)** | 6.4 (2.9) |
| AMCA | 9.0 (2.3)** | 8.1 (2.2) |
| gASCA | 8.3 (3.7)** | 6.4 (3.7) |

**$p < 0.00001$ versus Non-complicated disease course

TABLE 10

Regression analysis: significance of different marker for differentiation between CD patients with complicated disease vs. patients with non-complicated disease

| Variable | Coefficient | p |
|---|---|---|
| gASCA | 0.0231 | <0.0001 |
| ACCA | 0.0210 | <0.0001 |
| ALCA | 0.0203 | 0.0239 |
| CARD15 total number of variants | 0.0595 | 0.0246 |
| AMCA | — | Non significant |

TABLE 11

Diagnostics performance for differentiation between CD patients with complicated diseases and CD patients non-complicated disease course according to combination of gASCA and CARD15 variants and according to combination of gASCA, ACCA, ALCA and CARD15 variants

| | Sensitivity (%) | Specificity (%) | Positive predictive value (%) | Negative predictive Value (%) | Overall agreement (%) |
|---|---|---|---|---|---|
| Combination of gASCA, ALCA, ACCA, and CARD15 (cutoff = 0.54) | 44.8 | 80.1 | 79.1 | 47.1 | 57.9 |
| Combination of gASCA, and CARD15 (cutoff = 7.1) | 34.7 | 80.3 | 74.9 | 42.1 | 51.6 |

TABLE 12

Anti-glycan antibody levels in CD patients with need for surgery versus CD patients who do not need surgery.

| Antibodies | Anti glycan antibodies levels, $(EU)^{0.5}$ Mean (SD) | |
|---|---|---|
| | Need for surgery (n = 422) | No need for surgery (n = 333) |
| ALCA | 6.5 (2.0)* | 6.0 (2.0) |
| ACCA | 7.8 (3.4)** | 6.8 (3.1) |
| AMCA | 8.9 (2.3)* | 8.3 (2.1) |
| gASCA | 8.3 (3.6)** | 6.7 (3.9) |

**$p < 0.00001$ versus No need for surgery
*$p < 0.01$ versus No need for surgery

TABLE 13

Regression analysis: significance of different marker for differentiation between CD patients who need surgery vs. patients without need for surgery.

| Variable | Coefficient | p |
|---|---|---|
| gASCA | 0.0331 | <0.0001 |
| ACCA | 0.0156 | 0.0012 |
| ALCA | — | Non significant |
| CARD15 total number of variants | 0.089 | 0.0246 |
| AMCA | — | Non significant |

TABLE 14

Diagnostics performance for differentiation between CD patients with need for surgery and CD patients without need for surgery according to a combination of gASCA and CARD15 variants and according to combination of gASCA, ACCA and CARD15 variants

|  | Sensitivity (%) | Specificity (%) | Positive predictive value (%) | Negative predictive Value (%) | Overall agreement (%) |
|---|---|---|---|---|---|
| Combination of gASCA, ACCA, and CARD15 (cutoff = 0.52) | 30.7 | 90.0 | 71.9 | 59.5 | 60.2 |
| Combination of gASCA, and CARD15 (cutoff = 0.44) | 23.4 | 90.6 | 68.6 | 57.4 | 59.2 |

TABLE 16

Regression analysis: significance of different marker for differentiation between IBD patients and non-IBD patients.

| Variable | Coefficient | p |
|---|---|---|
| gASCA | 0.0262 | <0.0001 |
| ACCA | −0.0054 | 0.1081 |
| ALCA | 0.0420 | <0.0001 |
| CARD15 total number of variants | 0.0390 | 0.0177 |
| AMCA | 0.0139 | 0.0089 |

TABLE 15

Anti-glycan antibody levels in IBD patients versus non-IBD pateints

| | Anti glycan antibodies levels, $(EU)^{0.5}$ Mean (SD) | |
|---|---|---|
| Antibodies | IBD (n = 1225) | Non-IBD (n = 313) |
| ALCA | 5.9 (2.1)** | 4.1 (1.4) |
| ACCA | 6.9 (3.3) | 6.8 (2.6) |
| AMCA | 8.2 (2.3)** | 7.0 (1.8) |
| gASCA | 6.6 (3.9)** | 3.0 (1.4) |

**$p < 0.00001$ versus Non-IBD

TABLE 17

Diagnostic performance for differentiation between IBD patients with and non-IBD acconding to combination of gASCA versus combination of gASCA, ACCA, AMCA, ALCA and CARD15 variants

|  | Sensitivity (%) | Specificity (%) | Positive predictive value (%) | Negative predictive Value (%) | Overall agreement (%) |
|---|---|---|---|---|---|
| Combination of gASCA, ACCA, ALCA, AMCA and CARD15 (cutoff = 0.38) | 72.7 | 80.5 | 93.4 | 42.7 | 74.1 |
| Combination of gASCA and CARD15 (cutoff = 4.0) | 66.4 | 80.5 | 93.0 | 38.0 | 69.2 |

What is claimed is:

1. A method for distinguishing between complicated and non-complicated Crohn's disease in a subject, the method comprising, providing a test sample from a subject diagnosed with Crohn's disease;

detecting a level of an anti-Glc(β1,3)Glc(β) antibody (ALCA) in said sample by binding of said ALCA in said sample to a carbohydrate reagent comprising an isolated Glc(β1,3)Glc(β) glycan;

detecting a level of an anti-GlcNAc(β1,4)GlcNAc(β) antibody (ACCA) in said sample by binding of said ACCA in said sample to a carbohydrate reagent comprising an isolated GlcNAc(β1,4)GlcNAc(β) glycan;

detecting a level of an anti-mannan antibody (ASCA) in said sample by binding of said ASCA in said sample to a carbohydrate reagent comprising an isolated mannan;

detecting a level of an anti-Man(α1,3)Man(α) antibody (AMCA) in said sample by binding of said AMCA in said sample to a carbohydrate reagent comprising an isolated Man(α1,3)Man(α); and distinguishing a complicated disease course in said subject by detection of an elevated level of each of said ALCA, ACCA, ASCA, and AMCA in said test sample relative to a control reference sample from one or more individuals known to have non-complicated Crohn's disease.

2. The method of claim 1, wherein said test sample is serum.

3. The method of claim 1, wherein said antibodies are detected by an enzyme-linked immunosorbent assay (ELISA).

4. The method of claim 1, wherein said isolated Glc(β1,3)Glc(β) glycan, said isolated GlcNAc(β1,4)GlcNAc(β) glycan, said isolated mannan, and said isolated Man(α1,3)Man(α) mannan are attached to a solid phase.

5. The method of claim 1, wherein said complicated disease course comprises penetrating, fistulating, structuring, or fibrostenosing disease course.

6. The method of claim 1, further comprising detecting a level of at least one additional antibody indicative of Crohn's Disease in said sample, wherein said additional antibody is selected from the group consisting of an anti-Man($\alpha$1,6)Man ($\alpha$) antibody (AMBA), an anti-Man($\alpha$1,2)Man($\alpha$) antibody (AMNA), and an anti-$\alpha$-Man antibody (AMA).

7. The method of claim 6, wherein said method comprises detecting levels of two of said additional antibodies in said sample.

8. The method of claim 6, wherein said method comprises detecting levels of each of said AMBA AMNA, and AMA in said sample.

9. The method of claim 6, wherein said ASCA, said AMCA, said AMBA, said AMNA, and said AMA are IgG antibodies.

10. The method of 9, wherein said anti-Glc($\beta$1,3)Glc($\beta$) antibody (ALCA) is an IgG antibody and said anti-GlcNAc ($\beta$1,4)GlcNAc($\beta$) antibody (ACCA) is an IgA antibody.

* * * * *